United States Patent
Fraasch et al.

(12)

(10) Patent No.: US 11,612,424 B2
(45) Date of Patent: Mar. 28, 2023

(54) METHODS OF RECOGNIZING AND ELIMINATING ARCS AND ARC INDUCED PLASMA DURING ENERGY DELIVERY IN TISSUE

(71) Applicant: Medtronic, Inc., Minneapolis, MN (US)

(72) Inventors: Steven J. Fraasch, Maple Grove, MN (US); Trenton J. Rehberger, Minneapolis, MN (US); Qin Zhang, Shoreview, MN (US); Lynn A. Davenport, New Brighton, MN (US); Steven V. Ramberg, North Oaks, MN (US); Brian T. Howard, Minneapolis, MN (US); Mark T. Stewart, Lino Lakes, MN (US); Alexander J. Hill, Blaine, MN (US); John Vandanacker, Rockford, MN (US)

(73) Assignee: Medtronic, Inc., Minneapolis, MN (US)

( * ) Notice: Subject to any disclaimer, the term of this patent is extended or adjusted under 35 U.S.C. 154(b) by 525 days.

(21) Appl. No.: 16/676,586

(22) Filed: Nov. 7, 2019

(65) Prior Publication Data
US 2020/0138506 A1 May 7, 2020

Related U.S. Application Data

(60) Provisional application No. 62/756,810, filed on Nov. 7, 2018.

(51) Int. Cl.
*A61B 18/12* (2006.01)
*A61B 18/00* (2006.01)
*A61B 18/14* (2006.01)

(52) U.S. Cl.
CPC ...... *A61B 18/1206* (2013.01); *A61B 18/1492* (2013.01); *A61B 2018/00577* (2013.01);
(Continued)

(58) Field of Classification Search
None
See application file for complete search history.

(56) References Cited

U.S. PATENT DOCUMENTS

| 5,601,608 A | 2/1997 | Mouchawar |
| 5,713,935 A | 2/1998 | Prutchi et al. |

(Continued)

FOREIGN PATENT DOCUMENTS

| WO | 2016164930 A1 | 10/2016 |
| WO | 2016178697 A1 | 11/2016 |
| WO | 2017024123 A1 | 2/2017 |

OTHER PUBLICATIONS

International Search Report and Written Opinion dated May 12, 2020, for corresponding International Application No. PCT/US2019/060179; International Filing Date: Nov. 7, 2019 consisting of 10 pages.
(Continued)

*Primary Examiner* — Joanne M Rodden
*Assistant Examiner* — Nora W Rhodes
(74) *Attorney, Agent, or Firm* — Michael Best & Friedrich LLP

(57) ABSTRACT

Methods and systems for monitoring and modifying pulsed field ablation (PFA) energy delivery to prevent patient safety risks and/or delivery device failure. In particular, some embodiments provide methods and systems for detecting and preventing arcs and arc-induced plasma, and their causal events, during delivery of pulsed field ablation energy, as well as methods and systems for identifying conditions
(Continued)

leading to potential delivery device failure and correcting charge imbalance or asymmetry.

14 Claims, 23 Drawing Sheets

(52) U.S. Cl.
CPC ............ *A61B 2018/00642* (2013.01); *A61B 2018/00875* (2013.01); *A61B 2018/00886* (2013.01); *A61B 2018/00892* (2013.01)

(56) References Cited

U.S. PATENT DOCUMENTS

| | | | |
|---|---|---|---|
| 2013/0041355 A1* | 2/2013 | Heeren | A61B 18/14 606/5 |
| 2014/0309632 A1* | 10/2014 | Ogata | A61B 18/1492 606/34 |
| 2015/0150618 A1* | 6/2015 | Onik | A61B 18/00 606/41 |
| 2015/0182282 A1* | 7/2015 | Zemel | A61B 18/1206 606/41 |
| 2016/0000495 A1* | 1/2016 | Elliott | A61B 18/1445 606/34 |
| 2016/0058493 A1 | 3/2016 | Neal, II et al. | |
| 2017/0035499 A1* | 2/2017 | Stewart | A61B 18/1206 |
| 2017/0049513 A1* | 2/2017 | Cosman, Jr. | A61B 18/1206 |
| 2017/0245928 A1* | 8/2017 | Xiao | H03K 17/687 |
| 2017/0319851 A1* | 11/2017 | Athos | A61N 1/36017 |
| 2020/0022649 A1* | 1/2020 | Rodriguez | A61B 18/1492 |
| 2020/0107877 A1* | 4/2020 | Koblish | A61B 5/01 |

OTHER PUBLICATIONS

Julie M. Demolin, et al., Soft Thrombus Formation in Radiofrequency Catheter Ablation, Journal of Pacing and Clinical Electrophysiology, vol. 25, #8, Aug. 2002, Futura Publishing Co., Armonk, NY, 5 pages.

\* cited by examiner

| FFT Result | Response |
| --- | --- |
| Inside lobe levels are greater than nominal | Increase Pulse Width |
| Inside lobe levels are less than normal | Decrease Pulse Width |
| Outside lobe levels are greater than nominal | Increase Rise/Fall Time |
| Outside lobe levels are lower than nominal | Decrease Rise/Fall Time |

Initial Therapy w/ Ringing

METHODS OF RECOGNIZING AND ELIMINATING ARCS AND ARC INDUCED PLASMA DURING ENERGY DELIVERY IN TISSUE

CROSS-REFERENCE TO RELATED APPLICATION

This application claims the benefit of U.S. Application Ser. No. 62/756,810 filed Nov. 7, 2018.

FIELD

This disclosure relates to methods and systems for detecting and eliminating conditions conductive to arcing in blood and tissue by pulsed electric field ablation generators and medical devices. This disclosure also relates to methods and systems for identifying conditions leading to potential delivery device failure and correcting charge imbalance or asymmetry.

BACKGROUND

Cardiac arrhythmias disrupt normal heart rhythm and reduce cardiac efficiency. These arrhythmias can be treated using pulsed field ablation (PFA) or radiofrequency (RF) ablation therapy. The delivery of ablation therapy involves the use of a reliable, powerful, and precisely controlled electrical energy source in the form of high voltage pulse generator. These pulses are delivered to perform reversible or irreversible electroporation via an ablation therapy delivery device of intended cardiac sites. Reversible electroporation is used to reversibly permeabilize cells to catalyze acceptance of genes or drugs, whereas irreversible electroporation is used to create permanent and lethal nanopores which can electrically isolate target areas of the myocardium and prevent arrhythmias, such as atrial fibrillation.

PFA deliveries are very low in total energy yet intense in power, but PFA energy delivered through its intended pathway from equipment (for example, an ablation therapy delivery device such as an ablation catheter or surgical ablation clamp) to the patient has incumbent constraints and design challenges for reliable, safe transmission. One of the most important issues for the design of ablation therapy delivery systems is the balance between delivering an effective amount of energy and keeping the delivery device as small as possible. For example, it may be desirable to apply the highest voltage that can be delivered reliably and safely through the greatest number of delivery device electrodes applying endocardial PFA therapy, but the size of the delivery device must be minimized to facilitate patient safety and physician ease of use. In addition, electrode surface areas and gaps between electrodes may both need to be minimized to achieve higher quality recordings of intracardiac electrograms, thereby increasing current density on each electrode. Therefore, PFA therapy transmission efficacy and optimality is traded off against reliability, safety, and operability where the latter constraints must be maintained at acceptable levels of patient risk.

An example of an efficacy/reliability tradeoff is the selection of catheter wire diameter. Both conductor and insulation thickness must be optimally chosen to reliably convey high current and insulate against voltage breakdown in the face of constraints. Although an increased number of wires and/or an increased diameter of each wire enhances current and voltage capability of the delivery device, such increases also demand greater lumen diameter(s) which, in turn, increases wire-lumen friction and wear. To reduce friction to an acceptable level when an increased number of wires and/or increased wire diameter are used, the diameter of the delivery device lumen and/or the diameter of an introducer device used to position the delivery device is also increased. However, the increased diameter increases the potential for post-procedure vasculature bleeding complications, which must be minimized.

Further, although quality and longevity of the delivery device are expected, there is always a risk that a particular delivery device will fail before its expected useful life. Therefore, the delivery device must be monitored to ensure that excessive amounts of energy are not delivered through a dysfunctional device, which could not only further damage the device, but could also harm the patient. Furthermore, it is important that the user (for example, a physician) is notified if the delivery device is not functional or if there is a danger of device failure before each energy delivery.

The diameter of the delivery device is largely dictated by the electrical requirements and, therefore, the size of one or more lumens within the elongate body or shaft of the delivery device. As noted above, there are restrictive size requirements placed on the delivery device to ensure patient safety. However, such constraints may severely limit on the size and quantity of the wires within one or more lumens of the elongate body of the delivery device. As a result, the energy delivery pathway is vulnerable to degradation and eventual failure. For example, when PFA energy is delivered through the delivery electrodes of the device, an arc, and possibly an arc-induced plasma, may occur when one or more of the delivery electrodes come into proximity with other metal objects within the patient, such as the delivery device's guide wire, an auxiliary diagnostic catheter, or an implanted stent. An arc occurs when current passes through a typically non-conductive medium, and plasma may be produced as a result (such as visible light). For example, an arc may occur through blood between an energy delivery electrode and tissue. As arc events create extremely high current (~80 amps), very small-gauge wires within the delivery device may overheat and fail. By the I.M. Onderdonk equation, a series of 120 biphasic, 5-µs pulses at 21.6 amps per 38 gauge (4 mil) conductor can cause a copper wire to rise 80° C. from 20° C. ambient temperature, resulting in a 100° C. temperature inside the delivery device, which can rapidly damage the device. While a properly designed device used in a routine cardiac ablation procedure can be expected to provide nominal performance, a single arc event can render a catheter defective, requiring that the catheter be explanted and replaced, a procedure that lengthens the operation's time and increases its cost. Additionally, current spikes, which may be caused by reasons such as insufficient electrode spacing, may also produce bubbles, barotrauma, heat, and other undesirable side effects. Therefore, a PFA system that can detect conditions conducive to arcing, as well as possessing the means of adjusting generator parameters and/or advising the physician to adjust their positioning and manipulation of the device to prevent such an occurrence, greatly increases patient safety and reduces complexity, time, and cost of a PFA procedure.

However, some currently known monitoring and safety systems are limited. Systems that include internal impedance measuring devices can resolve pathway failures in devices, interconnecting cables, and generator systems. Indeed, low-power impedance measurements are useful for determining the condition of the energy delivery pathway. However, since impedance measurements are typically made at very low levels of radio frequency (RF) energy, they are not useful in recognizing arcs or plasma, which only occur during application of very high energy capable of creating high electric fields. Arcs or plasma occurring in blood, outside the device, can lead to the formation of heat, barotrauma, and/or bubbles and embolic material that have the potential of causing cerebrovascular ischemic injury. An arc can also create a shockwave and subsequent cavitation, where pressures are exerted on vasculature causing permanent damage. Therefore, it is imperative that the PFA system recognize an arc in its early formation, so that the sourcing condition is terminated immediately, and the arc event is relegated to inconsequential thermal and mechanical energy.

High voltage electroporation waveform generators (such as PFA generators) will generate pulses 10 whose shape and characteristics are, for example, generally as shown in FIG. 1. As a practical matter for pulsed field ablation, a tradeoff is made between shortening the rise time $\tau_r$ and/or the fall time $\tau_f$ (that is, the time it takes the waveform to rise from 10% to 90% or fall from 90% to 10% of the final amplitude, respectively) to reduce time spent at cellular sub-transmembrane potential and the propensity of short rise-fall times to cause overshoot and ringing. An example of a pulse 10 with severe overshoot and ringing is shown in FIG. 2.

A PFA generator may use metal oxide varistors to limit or clamp a waveform's voltage before it reaches a damaging level. A limitation of varistors, however, is that their thresholds for minimum and maximum actuation cover a wide span, typically 20% of their nominal rating. Thus, their actuation threshold can be either too low, such that the device begins to clamp at the intended level of therapy voltage and therefore limit the effectiveness of therapy, or too high, such that the arc occurs anyway. Varistors also add considerable capacitance to the waveform generator's source impedance, which distorts the therapy waveform and adds load reactance, which, in turn, encourages overshoot and ringing. Overshoot and ringing then imparts undesirable heat to the electroporated tissue. Last, a varistor can only clamp a voltage transient after it is produced and cannot apply a feedback to end the arc in its formation.

In some cases, the arc occurs due to an oscillation created by a waveform pulse with abnormally fast rise and fall times. As shown in FIG. 2, the lower horizontal line on the left-hand side of the pulse 10 is the desired PFA therapy potential (voltage), but the ring (more formally referred to as an oscillation) exceeds the therapy amplitude by a factor of approximately 3. An oscillation of this magnitude is likely related to an arc condition with commensurate heating of tissue, denaturing of blood proteins (forming embolic material), and possible damage to the delivery device and generator system.

In addition to potential device failure and size constraints associated with PFA systems, delivery of PFA energy to muscle tissue can also cause unintended muscle stimulation, which occurs when electrical charge builds up in the tissue. This unintended stimulation can be mitigated by using short, balanced, biphasic waveform pulses 12, wherein any charge accumulation from the first positive phase 12A of the biphasic waveform 12 is quickly cancelled by a pulse of opposite polarity (that is, the negative phase 12B of the biphasic waveform 12). For example, as shown in FIG. 23, the integrated current 14 has a charge of zero. However, even a slight asymmetry between the phases 12A, 12B may lead to incomplete cancellation of the charge (for example, as shown in FIG. 24).

One potential cause of asymmetry is the discharge of one or more capacitors of the PFA generator to power the delivery. PFA therapy can deliver an enormous amount of power over short periods of time (potentially dozens of kilowatts in pulses several microseconds long). A power supply capable of supplying that much power continually would be prohibitive, so energy is stored in a bank of capacitors before delivery. During delivery, current flows from the capacitor bank rather than from the power supply itself. Once a delivery is complete, the power supply can resume charging the capacitor bank. However, therapy voltage and delivery current will decrease as charge is depleted from the capacitor bank. Exaggerated, non-limiting examples of output current decrease are shown in FIGS. 25 and 26. In FIG. 26, the peak voltage of each subsequent pulse 12 (or phase pulse 12A, 12B) is slightly less than the peak voltage of the pulse before, leading to a net imbalance of delivered charge. The amount of reduction depends on the electrical current delivered and capacitance of the capacitor bank: a higher current will more rapidly deplete the energy stored in the capacitor banks, while a capacitor bank having a higher capacitance will offer a larger amount of stored energy. Unless mitigated, this will lead to an imbalance of charge accumulating in the direction of the first pulse's polarity (positive or negative).

Another potential cause is mismatched rise and/or fall times between polarities. An exemplary ideal PFA pulses would be a perfectly rectangular pulse, with impossibly sharp rising and falling edges. Limitations imposed by real components, however, result in non-zero actual rise and fall times. As a non-limiting example, consider an H bridge circuit 18 constructed from n-type metal-oxide semiconductor (nMOS) with transistors 20, such as metal-oxide-semiconductor field-effect transistors (MOSFETs) or insulated gate bipolar transistors (IGBTs), used to create biphasic PFA pulses (for example, transistors 20 are Q1, Q2, Q3, and Q4, as shown in FIG. 27). In order to deliver a pulse, a low-voltage "positive pulse enable" signal is sent from a digital control circuit into a gate driver integrated circuit (IC), which, in turn, is connected to the gate of a transistor 20. Voltage at the gate of the transistor 20 controls resistance between its drain and source, which creates the therapy pulse. However, the original digital signal is delayed slightly by the gate driver, the gate driver has a finite current capability which requires time to charge the transistor's parasitic gate capacitance, the drain-source resistance will reduce the total current delivered, and so on. These effects lead to wasted power in the PFA generator and reduced dwell time at the desired therapy voltage. Further, these effects may vary from component to component. If the components driving one polarity switch faster than those driving the other polarity, or if one polarity's transistor 20 has a significantly lower saturated drain-to-source resistance, charge will tend to accumulate in that polarity. For example, FIG. 28 shows the effect of mismatched rise times $\tau_{r\text{-}positive}$ and $\tau_{r\text{-}negative}$ between each half of the biphasic pulse (that is, between the positive phase pulse 12A and the negative phase pulse 12B), in which the negative phase takes longer to reach the nominal voltage and leads to a net positive charge.

SUMMARY

Some embodiments advantageously provide methods and systems for monitoring and modifying pulsed field ablation (PFA) energy delivery to prevent patient safety risks and/or delivery device failure. In particular, some embodiments provide methods and systems for detecting and preventing arcs and arc-induced plasma, and their causal events, during delivery of pulsed field ablation energy, as well as methods and systems for identifying conditions leading to potential delivery device failure and correcting charge imbalance or asymmetry.

A method including using at least one detector that measures the rise-fall time of a pulse in its early formation is described herein. If the measured rise-fall time is too short, feedback can be provided to the PFA generator's output stage to temporarily disable the sourcing energy responsible for the oscillation, but then increase the PFA generator's H bridge circuit's rise-fall time, such that the arc, or condition causing an arc, is eliminated for subsequent delivery pulses. As a result, the arc never occurs.

A second method includes using at least one detector that uses a precise, programmable threshold that suppresses the waveform if a voltage and/or amplitude threshold is reached and/or exceeded (see FIG. 2). As the threshold is reached and/or exceeded, a pulse is sent from a detector (or detector-comparator) that is processed within a few nanoseconds and sent as a "kill" signal to the PFA generator's output H bridge circuit.

A third method includes applying a mask to a delivered waveform to ensure that the therapy waveform's timing and amplitude characteristics fit the prescribed therapy waveform's dosing prescription. The purpose of this fitting is to detect an anomalous pulse prior to a subsequent pulse capable of arcing. The predictive period may be one pulse, many pulses, or a few deliveries consisting of many pulses until the eventual arc or catheter damage occurs.

A fourth method includes applying information gained using one or all three prior methods, and making an adjustment to the PFA generator's output circuit electronics, slowing the rise-fall time and/or reducing the delivery voltage, or interlocking and ceasing delivery altogether, to eliminate the arc on a subsequent pulse delivery.

A fifth method including applying information gained using one or all of the first three methods, and generating an electronic message advising the operating physician of the recommended course of action to remedy an arc condition that may exist due to a damaged or improperly manipulated catheter.

In one embodiment, a method of modifying pulsed field ablation (PFA) energy delivery comprises: delivering a PFA pulse from a PFA generator; measuring a rise time and a fall time of the PFA pulse; calculating a voltage of an oscillatory pole in the PFA pulsed based at least in part on rise time and the fall time; and modifying at least one of the rise time and the fall time to reduce the voltage of the at least one oscillatory pole in the PFA pulse.

In one aspect of the embodiment, the PFA generator further includes processing circuitry having an H bridge circuit.

In one aspect of the embodiment, modifying the at least one of the rise time and the fall time including adjusting an input resistance in the H bridge circuit.

In one aspect of the embodiment, modifying at least one of the rise time and the fall time includes reducing the time in which the PFA pulse reaches 90% of a final amplitude of the PFA pulse under heavily loaded conditions.

In one aspect of the embodiment, the at least one of the rise time and the fall time is modified to a time between 0.3 µs and 0.5 µs.

In one aspect of the embodiment, the method further comprises: measuring a pulse width of the PFA pulse; calculating a voltage of an oscillatory pole in the PFA pulse based at least in part on the pulse width; and modifying the pulse width to reduce the voltage of the at least one oscillatory pole in the PFA pulse.

In one aspect of the embodiment, the method further comprises ceasing delivery of the PFA pulse from the PFA generator when the calculated voltage of the oscillatory pole is greater than a threshold voltage.

In one embodiment, a method of modifying pulsed field ablation (PFA) energy delivery comprises: delivering at least one biphasic PFA pulse from a PFA generator, each of the at least one biphasic PFA pulse including a biphasic pair having a positive phase and a negative phase; and calculating a value of an integral of a current over the biphasic pair.

In one aspect of the embodiment, the method further comprises measuring a pulse width of the PFA pulse; and modifying the pulse width of the biphasic PFA pulse when the integral of the current has a non-zero value.

In one aspect of the embodiment, the method further comprises delivering a runt pulse in the biphasic PFA pulse and modifying the pulse width of the biphasic PFA pulse when the integral of the current has a non-zero value.

In one aspect of the embodiment, the runt pulse has an amplitude that is less than an amplitude of the positive phase of the biphasic pair.

In one aspect of the embodiment, the runt pulse has an amplitude that is less than an amplitude of the negative phase of the biphasic pair.

In one aspect of the embodiment, the runt pulse is delivered after the negative phase of the biphasic pair.

In one embodiment, a system for delivering pulsed field ablation (PFA) energy comprises: a delivery device including at least one energy delivery electrode; and a control unit in electrical communication with the delivery device, the control unit including a PFA generator. In this embodiment, the PFA generator has: an H bridge circuit, the H bridge circuit being configured to deliver PFA energy to the delivery device, the PFA energy including a plurality of pulses; a detector, the detector being in electrical communication with the H bridge circuit and configured to: measure a rise-fall time of each of the plurality of pulses; measure a pulse width of each of the plurality of pulses; determine a voltage of at least one pole occurring in at least one of the plurality of pulses; compare the determined voltage of the at least one pole to a threshold voltage; and at least one of: adjust at least one of the rise-fall time and the pulse width of at least one of the plurality of pulses by adjusting a voltage of the PFA energy produced by the H bridge circuit when the detector determines the determined voltage is greater than the threshold voltage; and prompt a use to lower an output level of the PFA generator.

In one aspect of the embodiment, the detector is an amplitude detector, the amplitude detector being configured to determine an amplitude of each of the plurality of pulses in a time domain.

In one aspect of the embodiment, the PFA generator further has a counter circuit in electrical communication with the amplitude detector.

In one aspect of the embodiment, the amplitude detector is configured to initiate a time count by a timer circuit, the rise-fall time being determined at least in part by the time count.

In one aspect of the embodiment, the PFA generator further has a spectrum detector, the spectrum detector being configured to determine the voltage of the at least one pole occurring in at least one of the plurality of pulses in the spectral domain.

In one aspect of the embodiment, the control unit being further configured to determine that a fault condition exists in the delivery device, the determination that a fault condition exists being based at least in part on a determined amplitude of at least one of the plurality of pulses.

In one aspect of the embodiment, the control unit is further configured to: determine an accumulated amount of charge delivered by the PFA generator; and when the determined accumulated amount of charge has a non-zero value, at least one of: adjust the pulse width of at least one of the plurality of pulses until the determined accumulated amount of charge has a zero value; and deliver at least one runt pulse until the determined accumulated amount of charge has a zero value.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

Figure 1:
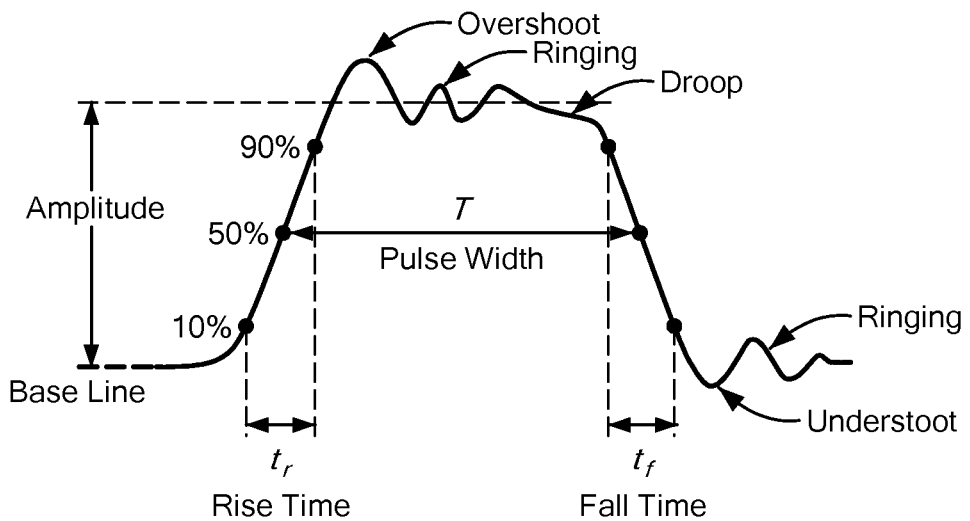
FIG. 1 is an illustration of pulsed field ablation (PFA) pulse characteristics.

Before describing in detail exemplary embodiments, it is noted that the embodiments reside primarily in combinations of apparatus components and processing steps related to delivering pulsed field ablation energy. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

The step response of a low order electrical pulse generator, such as a pulsed field ablation (PFA) generator 22, is well characterized by its 10%-90% rise-fall time. As shown in FIG. 1, the rise time, $t_r$, extends between 10% and 90% of the amplitude and the fall time, $t_f$, extends between 90% and 10% of the amplitude. The rise time and the fall time are collectively referred to herein as "rise-fall time" ($\tau$ or $\tau_r/\tau_f$), unless one differs or is adjusted differently than the other. Given that the system follows a first order resistive-capacitive or Gaussian system, the output should settle smoothly to a steady-state value with minimal overshoot (typically less than 20%) and no ringing. An example of a nominal PFA biphasic waveform 12 is shown in FIG. 1.

Figure 2:
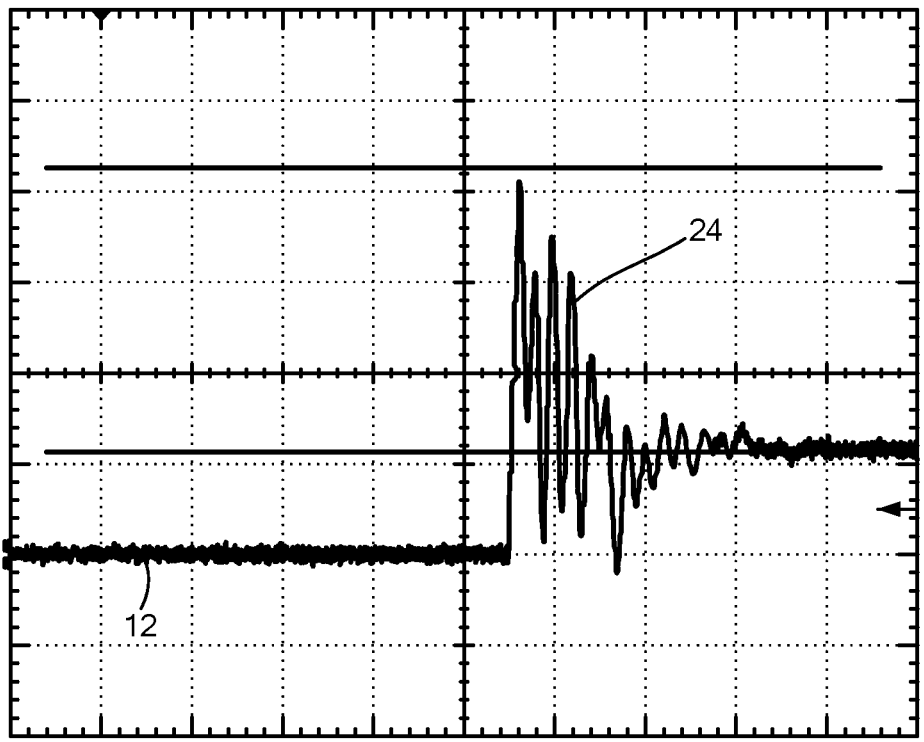
FIG. 2 is a graphical representation of a PFA pulse with severe overshoot (three times amplitude) and ringing.
Figure 3:
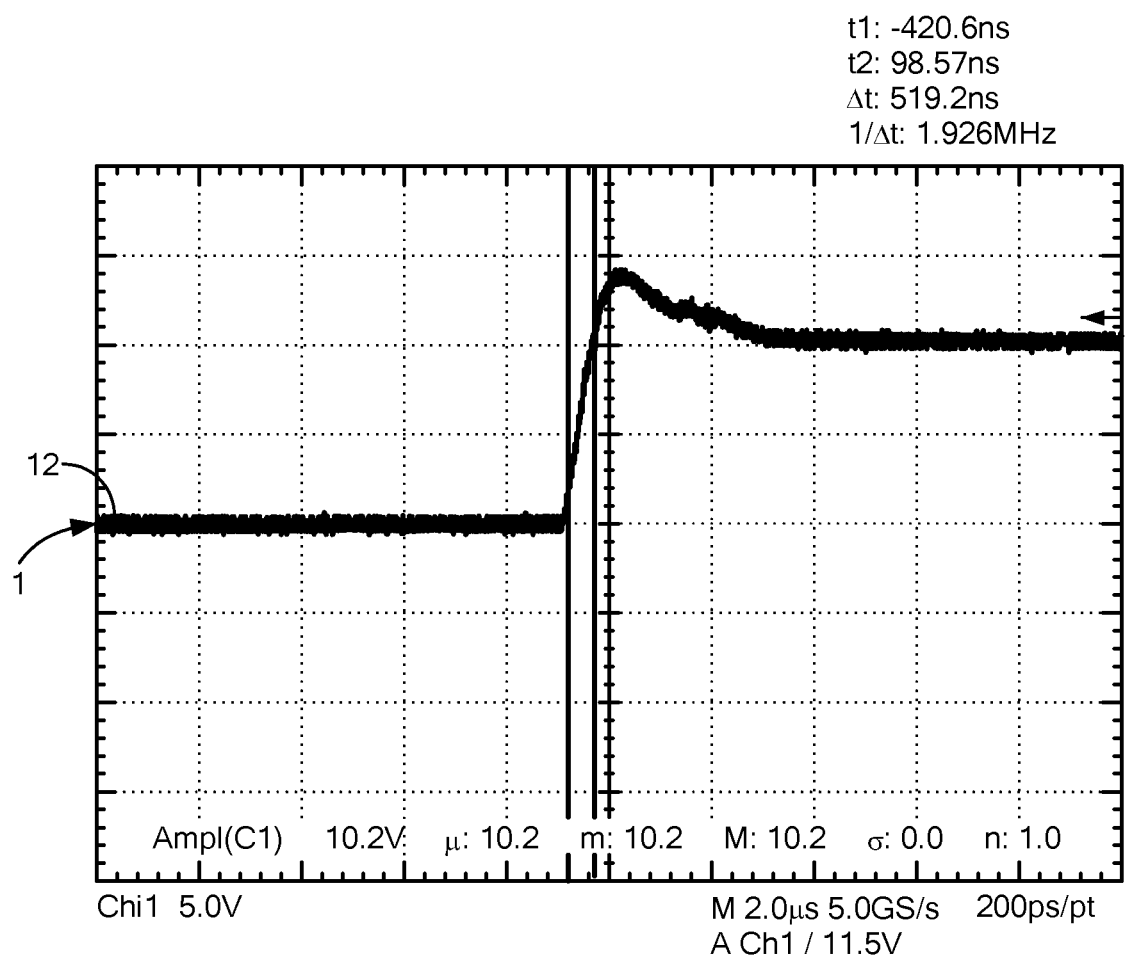
FIG. 3 is a graphical representation of an increased generator output system rise time to eliminate ringing.
Figure 12:
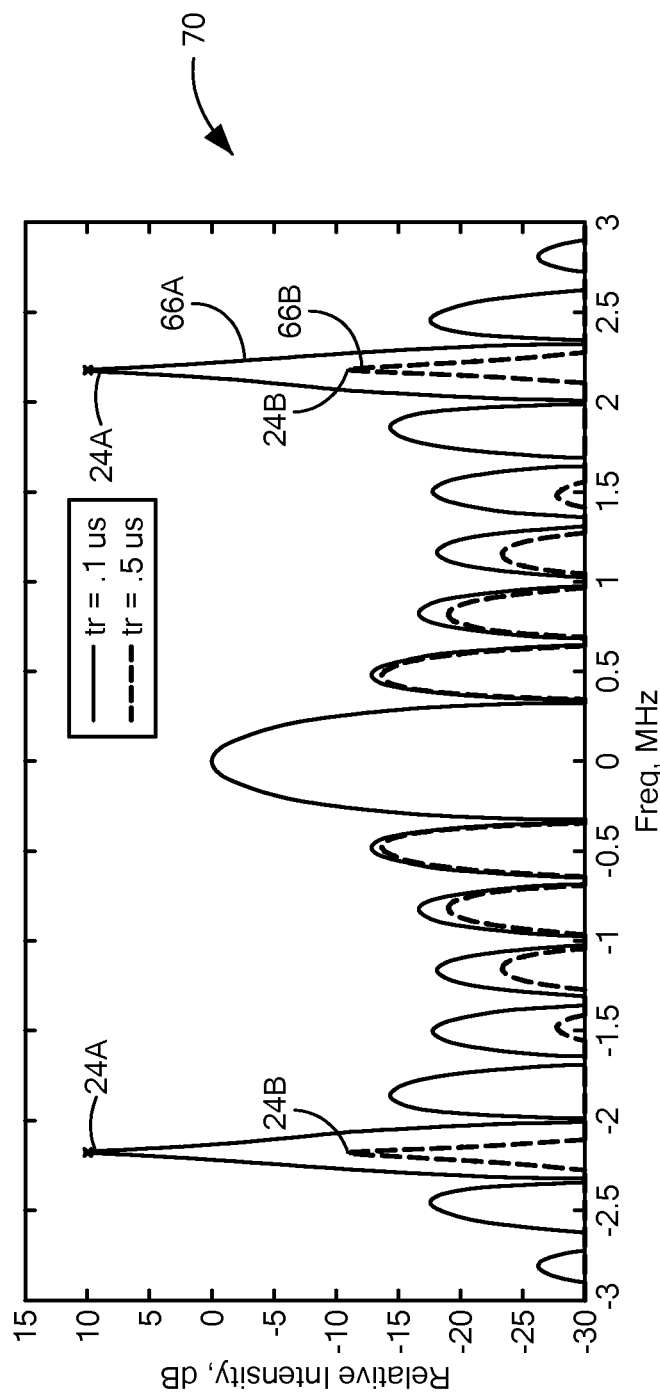
FIG. 12 is a graphical comparison of trapezoidal pulse spectrums containing 2.18 MHz poles, the first pulse spectrum having a rise-fall time of $\tau=0.1$ μs and the second pulse spectrum having a rise-fall time of $\tau=0.5$ μs.
Figure 15:
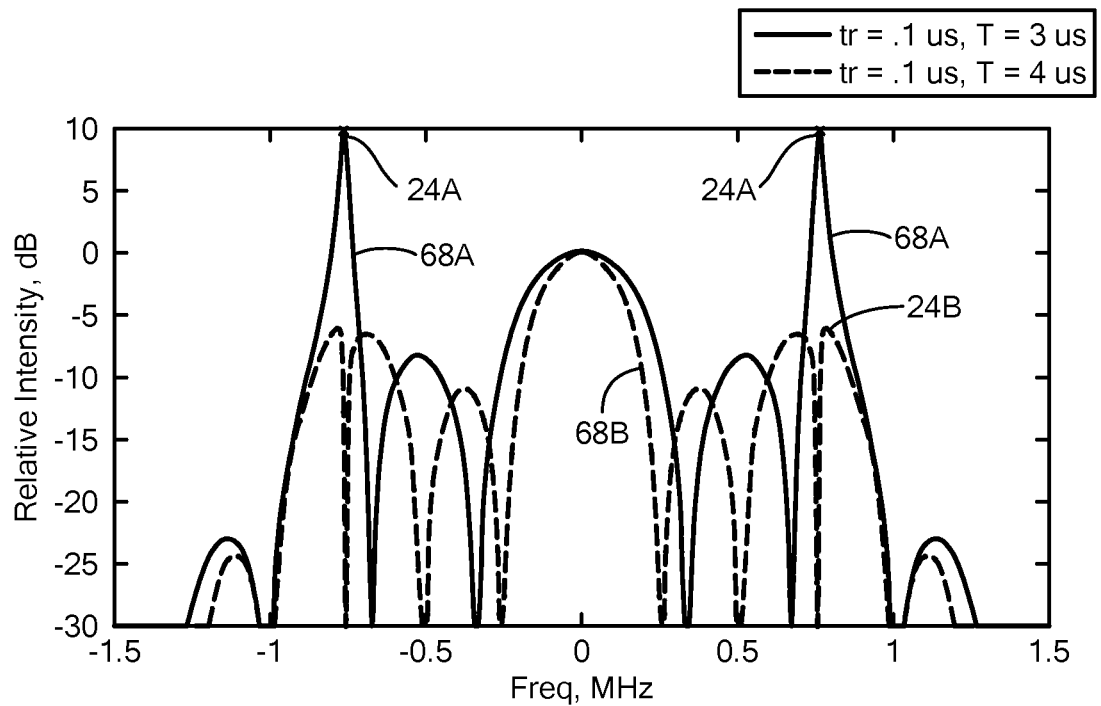
FIG. 15 is the graphical comparison of the pulse spectrums of FIG. 14, but with poles located at $s_{1+/-}=-2\pi e6$ (0.025+/−0.755) rads/sec.

Yet, as the rise-fall time $\tau$ of the pulse 12 decreases, the bandwidth of the pulse 12 increases, and additional in-band poles 24 are revealed that store, rather than dissipate, energy (for example, as shown in FIG. 12, where the pulses are designated with reference number 66, and FIG. 15, where the pulses are designated with reference number 68). The stored energy is then released and superimposed on the intended pulse, resulting in high, and possibly damaging, overshoot and ringing (for example, as shown in FIG. 2). However, the method disclosed herein includes purposely adjusting the PFA waveform rise and/or fall times $\tau_r$ and $\tau_f$ to be as short as possible to minimize imparted energy in the form of heat, while avoiding rise-fall time that create waveform overshoot and ringing. For example, excessive ringing (such as four times the amplitude) and overshoot may be caused by a rise-fall time that is too fast, and can lead to damage to the delivery device, the waveform or pulse generator (which may also be referred to herein as the PFA generator), and electrical and mechanical components of the delivery device and PFA system, and can potentially cause the formation of coagulants, bubbles, and char, which may present an embolism risk to the patient. A pulse 12 from the same PFA generator as in FIG. 2 is shown in FIG. 3, except where the pulse's rise time $\tau_r$ is lengthened to approximately 500 ns (from less than 100 ns in FIG. 2) to eliminate ringing.

Figure 4:
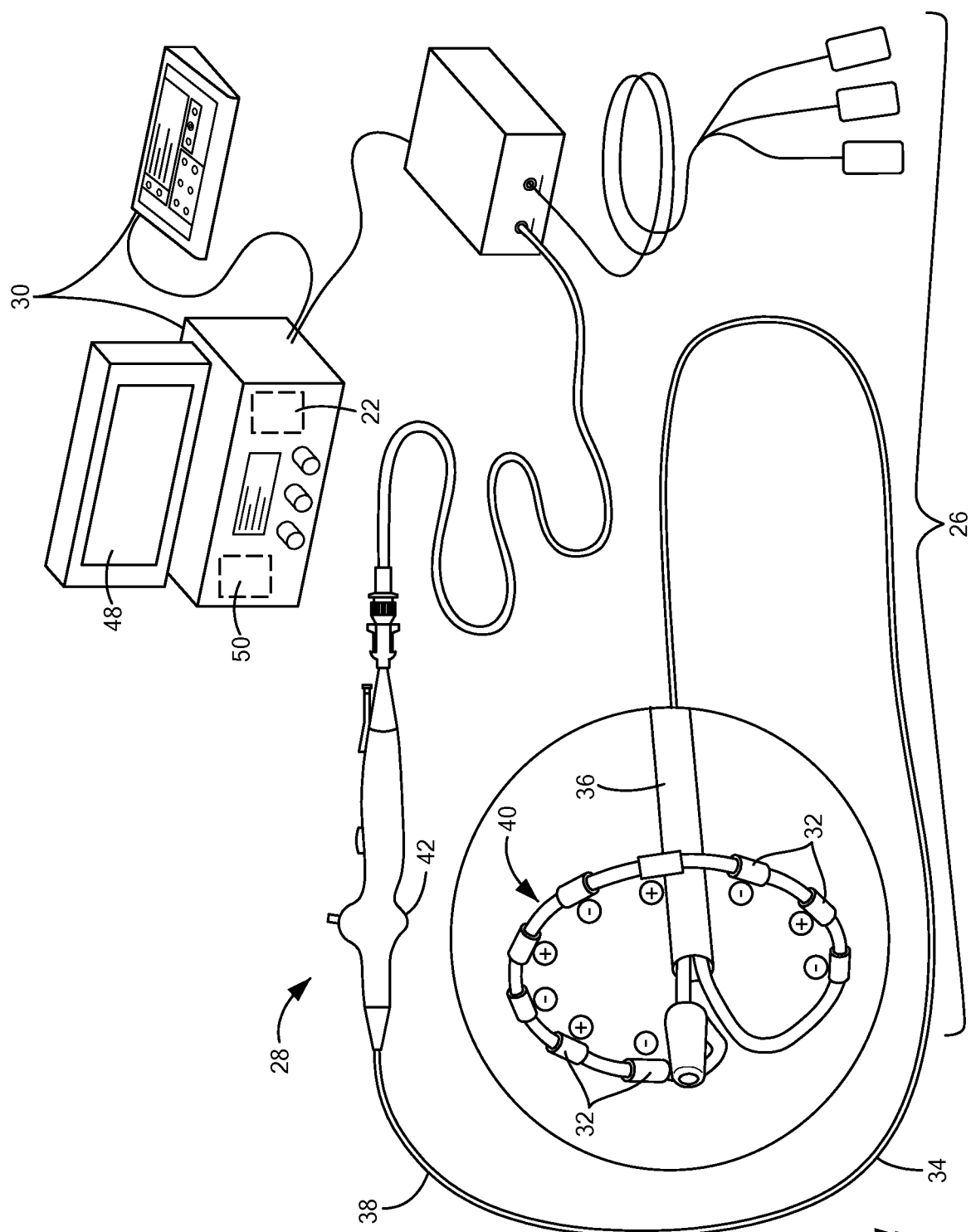
FIG. 4 is an exemplary PFA system.

Referring now to FIG. 4, an exemplary PFA system 26 is shown. The PFA system 26 may be used to treat endocardial surfaces, but it will be understood that the PFA system 26 may be used to treat other areas, including epicardial tissue, esophageal tissue, dermal tissue, tumors, or any other tissue that is treated with the application of PFA energy. In one embodiment, the PFA system 26 generally includes a delivery device 28 and a control unit 30.

The delivery device 28 may have any suitable size, shape, or configuration, but includes at least one energy delivery electrode 32 for delivering an electrical current, and may further include one or more electrodes such as mapping electrodes and/or electrodes for measuring characteristics such as impedance (not shown). In the non-limiting example shown in FIG. 4, the delivery device 28 includes an elongate body 34 with a distal portion 36 and a proximal portion 38, one or more lumens within the elongate body (not shown), and a flexible, expandable distal array 40 coupled to the distal portion 36 of the elongate body 34 and bearing a plurality of energy delivery electrodes 32. The plurality of energy delivery electrodes 32 are in electrical communication with the control unit 30. The delivery device 28 includes a handle 42 with one or more actuators for, for example, electrically and/or mechanically communicating with one or more steering elements within the delivery device 28 for maneuvering the distal array 40 to a target treatment location within the patient's body. The delivery device 28 may also include one or more sensors 44 (for example, associated with each energy delivery electrode, within one or more lumens of the elongate body 34, and/or at other locations in the delivery device 28 and/or control unit 30), such as temperature sensors, pressure sensors, piezoelectric elements, strain gauges, and/or fiber Bragg sensors.

The term "control unit" may be used to generally refer to any system components that are not part of the delivery device 28. The control unit 30 may be described to include components that are physically located within or integrated with the control unit 30 or are in communication with the control unit 30. In one embodiment, the control unit 30 includes a pulse or waveform generator (referred to herein as a PFA generator 22) that is in electrical communication with the energy delivery electrode(s) 32 of the delivery device 28 and configured to deliver pulsed field electrical energy for the treatment of tissue using pulsed field ablation (PFA). In some embodiments, the PFA generator 22 and the control unit 30 are the same component. The PFA generator 22 is configured to deliver high-frequency, non-ablative pulses for causing reversible and/or non-reversible electroporation in targeted tissue cells. For example, the PFA generator 22 may be configured to deliver ablative energy pulses in the range of approximately 0.1 microsecond to 100 microseconds in duration and at frequencies of approximately 20 Hz to 2000 Hz. In one embodiment, the PFA generator 22 and/or control unit 30 is configured such that the user is able to modulate or adjust one or more characteristics of the pulses 12, such as rise-fall time $\tau$ and/or pulse width T. Optionally, the PFA generator 22 may also be configured to deliver ablative energy (such as radiofrequency (RF) energy, laser energy, microwave energy, or the like) or the control unit 30 may include an additional energy generator for providing ablative energy).

In one embodiment, the control unit 30 also includes a user interface by which the user may select the energy delivery mode, monitor energy delivery parameters, adjust or stop energy delivery, select one or more energy delivery electrodes with which to deliver energy, or the like. For example, the user interface may include a foot pedal, mouse, joystick, one or more computers having one or more displays, buttons, knobs, touchpads, touchscreens, or other communication and/or input means 48. Although the PFA generator 22 and/or control unit 30 may be able to operate in a completely automated manner, the PFA generator 22 and/or control unit 30 may be configured to allow the user to assume control over energy delivery and/or to select, initiate, or otherwise assist the semi-automatic operation of the PFA system 26. Additionally, the PFA system 26 may optionally include one or more components such as a navigation system, mapping system, imaging system, delivery device electrode distribution system, remotes, or the like.

Figure 5:
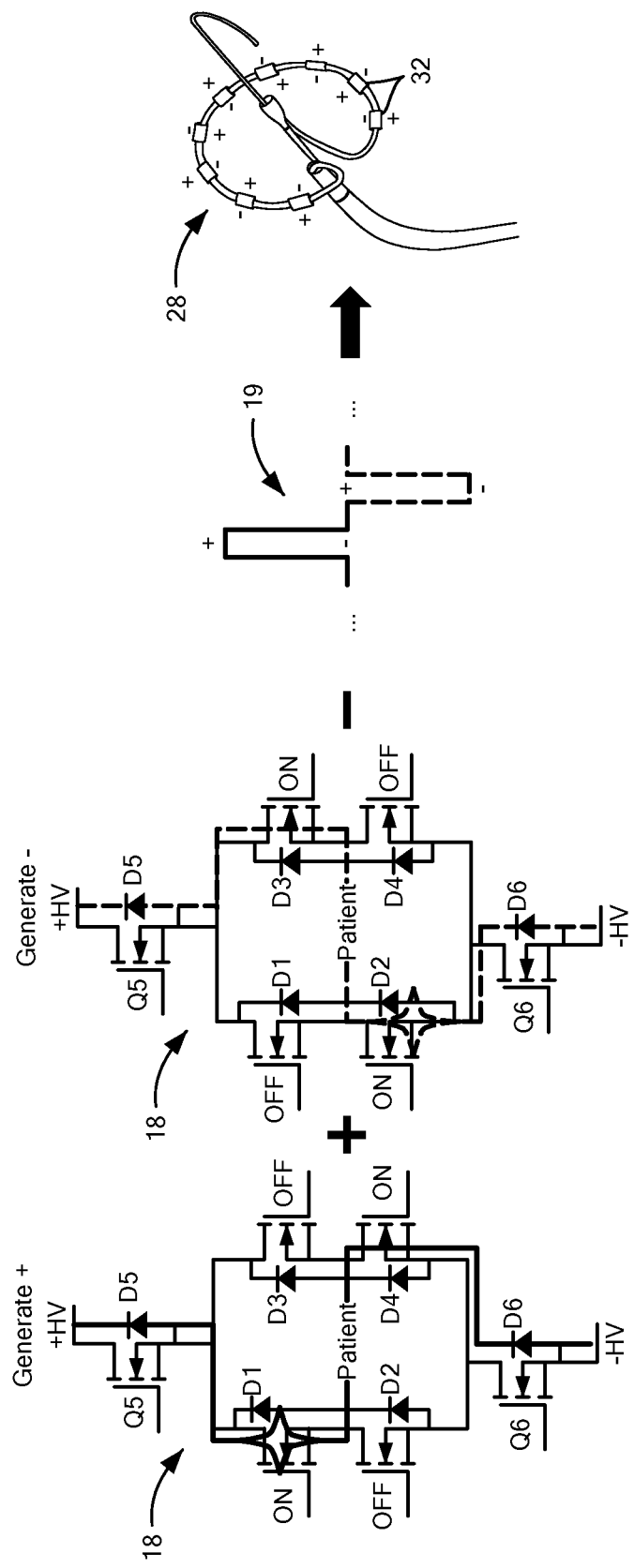
FIG. 5 shows an exemplary half bridge circuit (H bridge circuit) and transmission of an exemplary biphasic pulse pair generated by the H bridge system to an exemplary delivery device.

The control unit 30 and/or PFA generator 22 may further include processing circuitry 50 programmed to receive, process, and/or communicate data received from the delivery device 28 and/or other components of the PFA system 26. In one embodiment, the PFA generator 22 includes a power source 52 and processing circuitry 50 including an H bridge circuit, such as the H bridge circuit 18 shown in FIG. 5. In one embodiment, the H bridge circuit 18 generates positive and negative pulses to create a biphasic waveform 19 that is then transmitted to the energy delivery electrodes 32 of the delivery device 28. The energy delivery electrodes 32 then transmit the biphasic waveform (PFA energy) to the targeted tissue. The PFA generator 22 and/or the control unit 30 may also include processing circuitry 50 including one or more detectors, counters, or other circuits, such as those discussed below.

Figure 6:
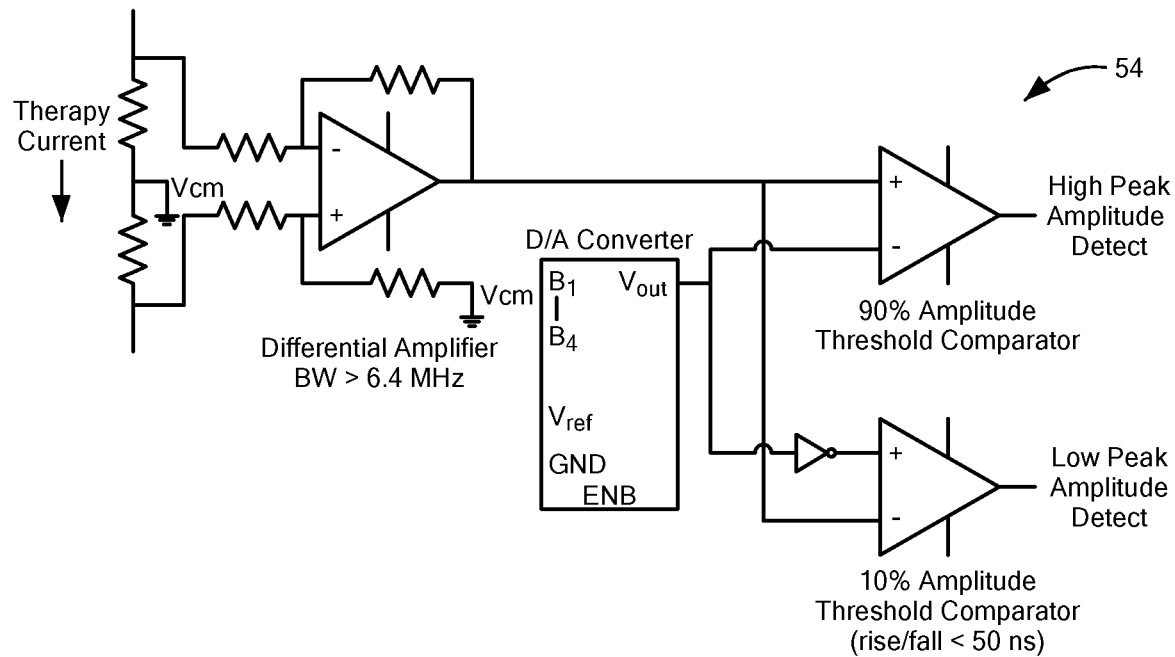
FIG. 6 is an exemplary amplitude detector.
Figure 7:
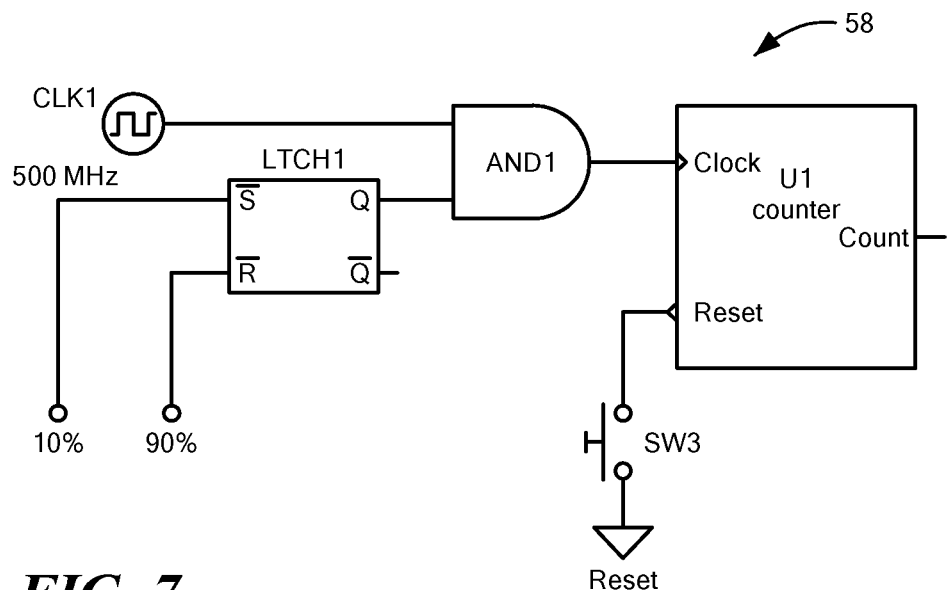
FIG. 7 is an exemplary counter circuit.

The PFA system 26 also includes at least one detector, which may be integrated with or external to the PFA generator 22. In one embodiment, the rise-fall time $\tau$ is determined by the at least one detector using time domain. In this embodiment, the PFA system 26 includes an amplitude detector 54, such as the amplitude detector 54 shown in FIG. 6, that detects the 10% and 90% amplitude of a pulse 12 (such as a trapezoidal pulse) delivered by the PFA generator 22 and initiates a time count by a counter circuit 58 (for example, as shown in FIG. 7) that determines the rise and/or fall time of the pulse 12. The amplitude detector 54 and counter circuit 58 are together also configured to apply a correction signal based on the determined rise-fall time to change the input base or gate resistance of the H bridge circuit 18. As the input base or gate resistance increases, the gate or base time constant of the RC circuit will increase, and the rise-fall time of the pulse will similarly increase. As will be shown, the effect of slowing rise-fall time will be to greatly attenuate or reduce undesirable overshoot and ringing. Additionally or alternatively, the amplitude detector 54 and counter circuit 58 are configured to apply a correction signal to adjust the pulse width T.

Figure 8:
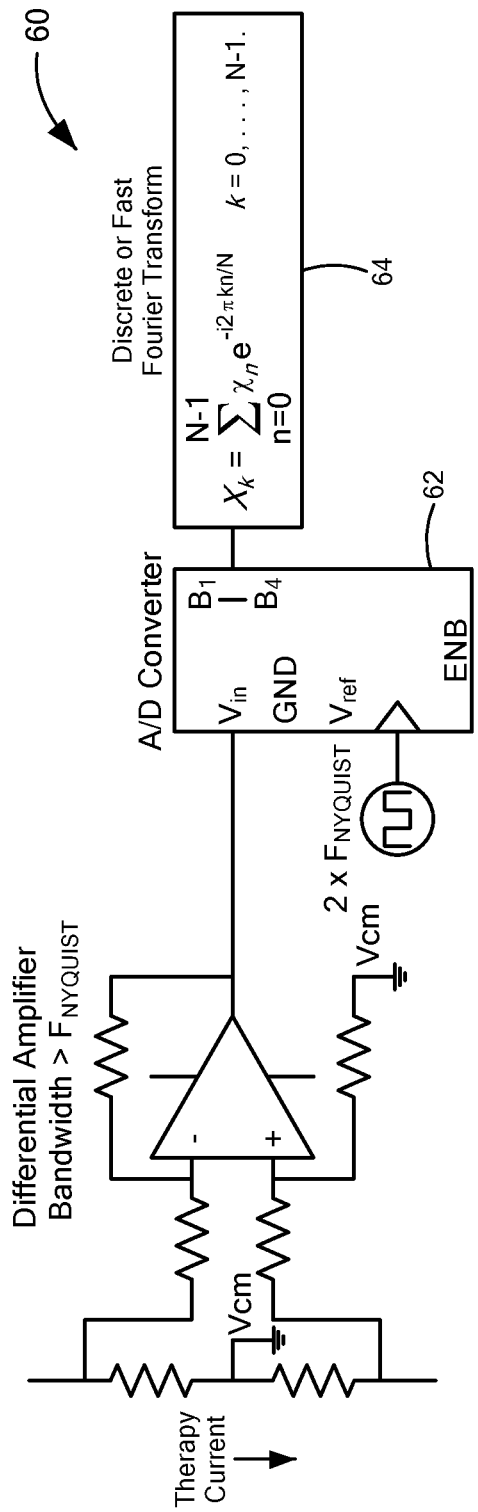
FIG. 8 is an exemplary spectrum analyzer.
Figure 9:
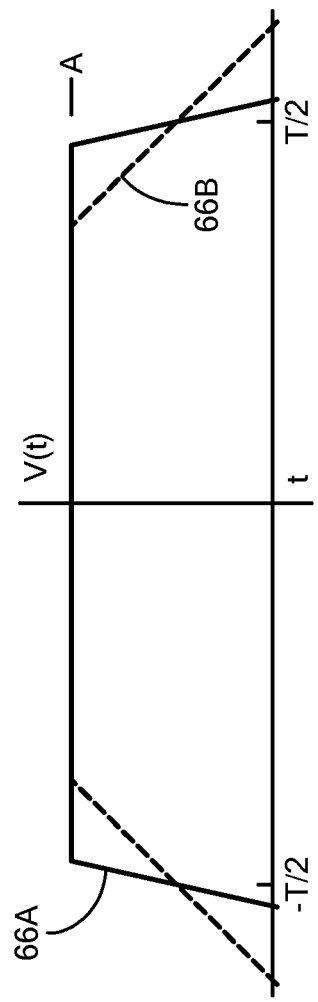
FIG. 9 is a graphical comparison of two trapezoidal pulses in the time domain.
Figure 10:
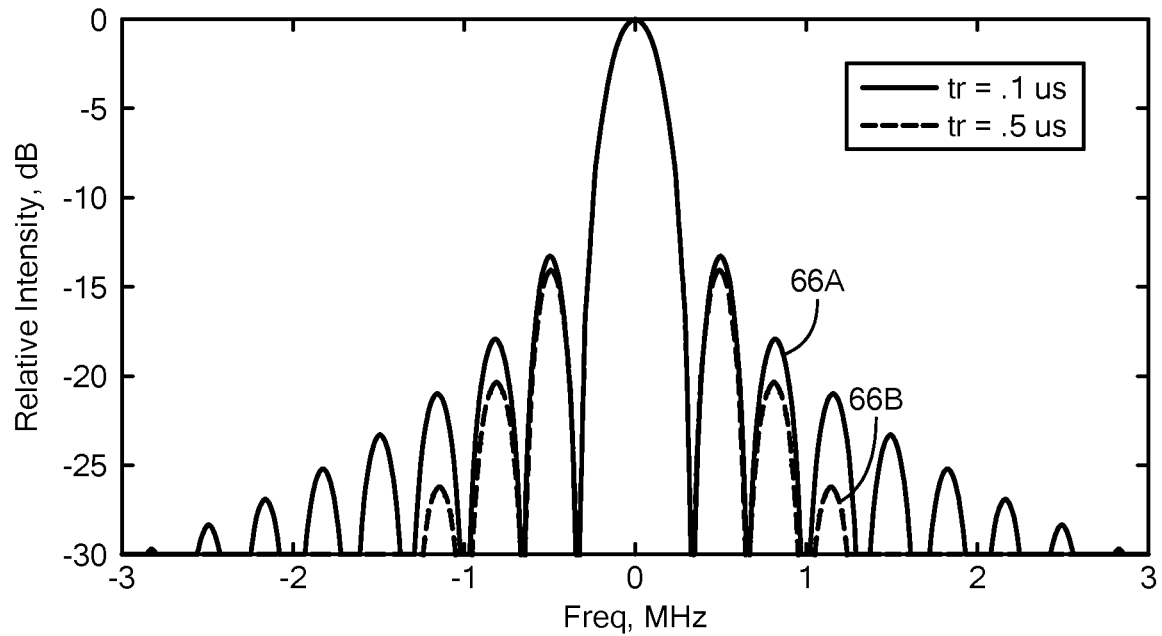
FIG. 10 is a graphical comparison of trapezoidal pulse spectrums (that is, trapezoidal pulses in the spectral domain), the first pulse spectrum having a rise-fall time of $\tau=0.1$ μs and the second pulse spectrum having a rise-fall time of $\tau=0.5$ μs.

Additionally or alternatively, poles 24 are identified by the at least one spectrum analyzer 60 (for example, the spectrum analyzer 60 shown in FIG. 8) using spectral domain. In this embodiment, the PFA system 26 includes a spectrum detector 60 having an analog-to-digital (A/D) converter 62 that applies a discrete or fast Fourier transform (FFT) 64 on the delivered current to identify oscillatory poles and/or excessively high side lobes 24 in the frequency spectrum of the pulse. For example, FIG. 9 shows a comparison of two trapezoidal pulses in the time domain, the trapezoidal pulses having different rise-fall times $\tau$ (0.1 µs and 0.5 µs), but the same pulse width T (3 µs). FIG. 10 shows a comparison between the two trapezoidal pulse spectrums ($\tau$=0.1 µs, or fast pulse 66A, and $\tau$=0.5 µs, or slow pulse 66B), and FIG. 10 shows a comparison between the two trapezoidal pulse spectrums of FIG. 10.

Mathematically, a trapezoidal pulse may be expressed as the convolution of two dissimilar width square pulses:

$$u(t) = \left(\frac{A}{\tau}\right) rect\left(\frac{t}{\tau}\right) \otimes rect\left(\frac{t}{r}\right) \tag{1}$$

$$U(f) = T\, sinc\,(f\tau)\, sinc\,(fT) \tag{2}$$

where A is the pulse amplitude, $\tau$ is the rise and fall time, and T is the pulse width. The Bode plot magnitude response for Equation (2) in the trapezoidal pulse frequency spectrum is show in FIG. 11, where both amplitude and frequency are plotted on logarithmic axes. The first response breakpoint is proportional to the trapezoidal pulse width and occur at frequency $$f = \frac{1}{\pi T},$$

or for a 3 µs wide pulse: f=106 KHz. The response then falls at −20 dB/decade until the next breakpoint (which is proportional to the trapezoidal pulse's rise/fall time) at frequency $$f = \frac{1}{\pi \tau},$$

or for a 0.25 µs rise/fall time characteristic: f=1.27 MHz. After the second breakpoint, the response continues to diminish at −40 dB/decade.

In the first method of reducing ringing, the rise-fall time $\tau$ (also referred to as $\tau_r/\tau_f$) is adjusted. Two time domain trapezoidal pulses 12 with different rise-fall times, $\tau$, are shown in FIG. 9. For the first time domain trapezoidal pulse 66A, $\tau$=0.1 µs. For the second time domain trapezoidal pulse 66B, $\tau$=0.5 µs. The pulse width for both is $\tau$=3 µs. The frequency spectrums of the two pulses 66A, 66B are compared in FIG. 10. It is noted that the second trapezoidal pulse 66B has a wider spectral width than the first trapezoidal pulse 66A. Further, the faster pulse 66A (that is, where $\tau$=0.1 µs) has a much greater propensity to ring or create large amplitude oscillations 24 than the slower pulse 66B (that is, where $\tau$=0.5 µs).

As shown in FIG. 2, a typical PFA generator 22 will contain energy delivery pathway imperfections that will result in energy storage and subsequent transfer of large oscillations to energy delivery electrodes 32 of the delivery device 28. These imperfections are referred to as "poles" 24, and must have their oscillatory effect minimized to avoid causing an in vivo arc as well as avoid damage to the PFA system 26. Next, it will be shown that the faster pulse 66A (that is, where $\tau$=0.1 µs) has a much greater propensity to ring or create large amplitude oscillations 24 than does the slower pulse 66B (that is, where $\tau$=0.5 µs).

As a modification to Equation (2) above, a transfer function expressing energy delivery electrode potential in time, but including two underdamped poles (that is, poles that are dampened incompletely to allow for some oscillations) will be:

$$u(t) = \left(\frac{A}{\tau}\right) rect\left(\frac{t}{\tau}\right) \otimes rect\left(\frac{t}{r}\right) + c_1 e^{s_2 + t} + c_2 e^{s_1 - t} \tag{3}$$

where the two pole locations are:

$$s_{1+/-} = -\sigma_1 +/- j\omega_{d1} \text{ rads/sec} \tag{4}$$

As an example, consider a system where two poles, $s_{1+/-}$, are located at:

$$s_{1+/-} = -2\pi e6(0.15+/-2.18j) \text{ rads/sec} \quad (5)$$

The two systems otherwise remain different only by their rise-fall times, that is, $\tau=0.1$ μs versus $\tau=0.5$ μs.

As a result of the poles 24 (which are shown as "Xs" in FIG. 12), the $\tau=0.1$ μs rise-fall time system stimulates 2.18 MHz oscillations (or ringing) that are approximately three times higher in voltage (10 dB) than the DC steady-state value (main lobe at 0 dB). In contrast, the $\tau=0.5$ μs rise-fall time system causes oscillations that are approximately 3.55 times less (−11 dB) than the DC steady-state value, or approximately 10.6 times less than the oscillations produced by the $\tau=0.1$ μs rise-fall time PFA system. Of note, the oscillatory poles 24B in the slow pulse 66B ($\tau=0.5$ μs) are dampened more effectively than the oscillatory poles 24A in the fast pulse 66A ($\tau=0.1$ μs). Therefore, by increasing pulse rise-fall time $\tau$ to an acceptable level, the ringing that produces embolic material and causes stroke may be reduced or eliminated. Increasing pulse rise-fall time $\tau$ in this manner also protects PFA equipment from damage.

Figure 13:
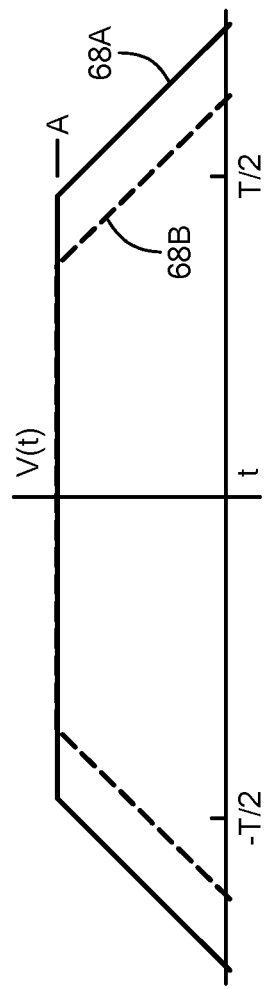
FIG. 13 is a graphical comparison of two trapezoidal pulses in the time domain, the trapezoidal pulses having the same rise-fall time $\tau$ and different pulse widths T.
Figure 14:
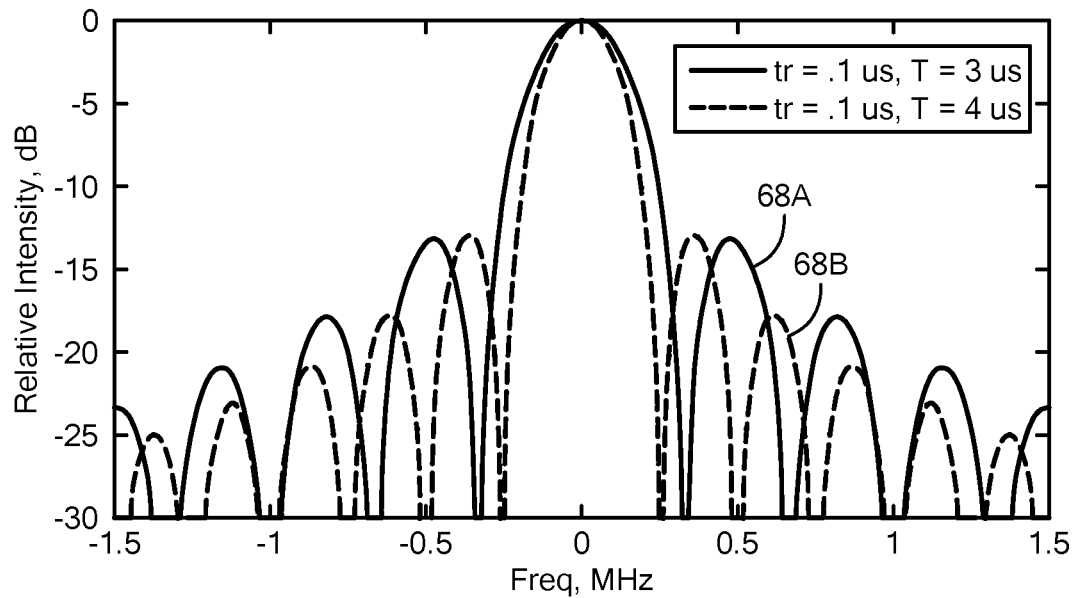
FIG. 14 is a graphical comparison of trapezoidal pulse spectrums (that is, trapezoidal pulses in the spectral domain), the first pulse spectrum having a pulse width of T=3 μs and a rise-fall time of $\tau=0.1$ μs, and the second pulse spectrum having a pulse width of T=4 μs and a rise-fall time of $\tau=0.1$ μs.

A second method of reducing ringing includes of adjusting the pulse width parameter, T, to cause pole(s) 24 to occur at area(s) on the trapezoid pulse waveform 12 that are at minima between sidelobes, or null(s). In this case, the rise-fall time is left unchanged at $\tau=0.1$ μs, but the pulse width T is increased from 3 to 4 μs. FIG. 13 is a graphical comparison of two trapezoidal pulses 68A, 68B in the time domain, with both pulses having the same rise-fall time $\tau$ but different pulse widths T. One pulse 68A has a pulse width of T=3 μs and the other pulse 68B has a pulse width of T=4 μs. FIG. 14 shows a comparison of two pulse spectrums, each having a rise-fall time of $\tau=0.1$ μs, without poles where the spectral sidelobes are purposely misaligned. The first pulse 68A has a pulse width of T=3 μs and the second pulse 68B has a pulse width of T=4 μs. FIG. 15 then exploits this property and compares the effect of poles 24 located at:

$$s_{1+/-} = -2\pi e6(0.025+/-00755j) \text{ rads/sec} \quad (6)$$

FIG. 15 reveals that increasing pulse width to 4 μs in pulse 68B, but otherwise leaving the rise-fall time unchanged at $\tau=0.1$ μs, reduces the PFA system's 755 KHz ringing amplitude substantially by a factor of 6.31 times (−16 dB) compared to using a 3 μs PFA pulse width T, as in pulse 68A. That is, the poles 24A in pulse 68A, which has a smaller pulse width, are approximately six times greater than the poles 24B in pulse 68B, which has a greater pulse width.

Thus, two methods are discussed above for reducing PFA waveform oscillations: adjusting the rise-fall time $\tau$ and adjusting the pulse width T. However, a hybrid approach may be used where both the rise-fall time $\tau$ and the pulse width T are adjusted to reduce ringing. Adjusting the rise-fall time $\tau$ and the pulse width T has the same effect as removing energy from the poles.

Figure 16:
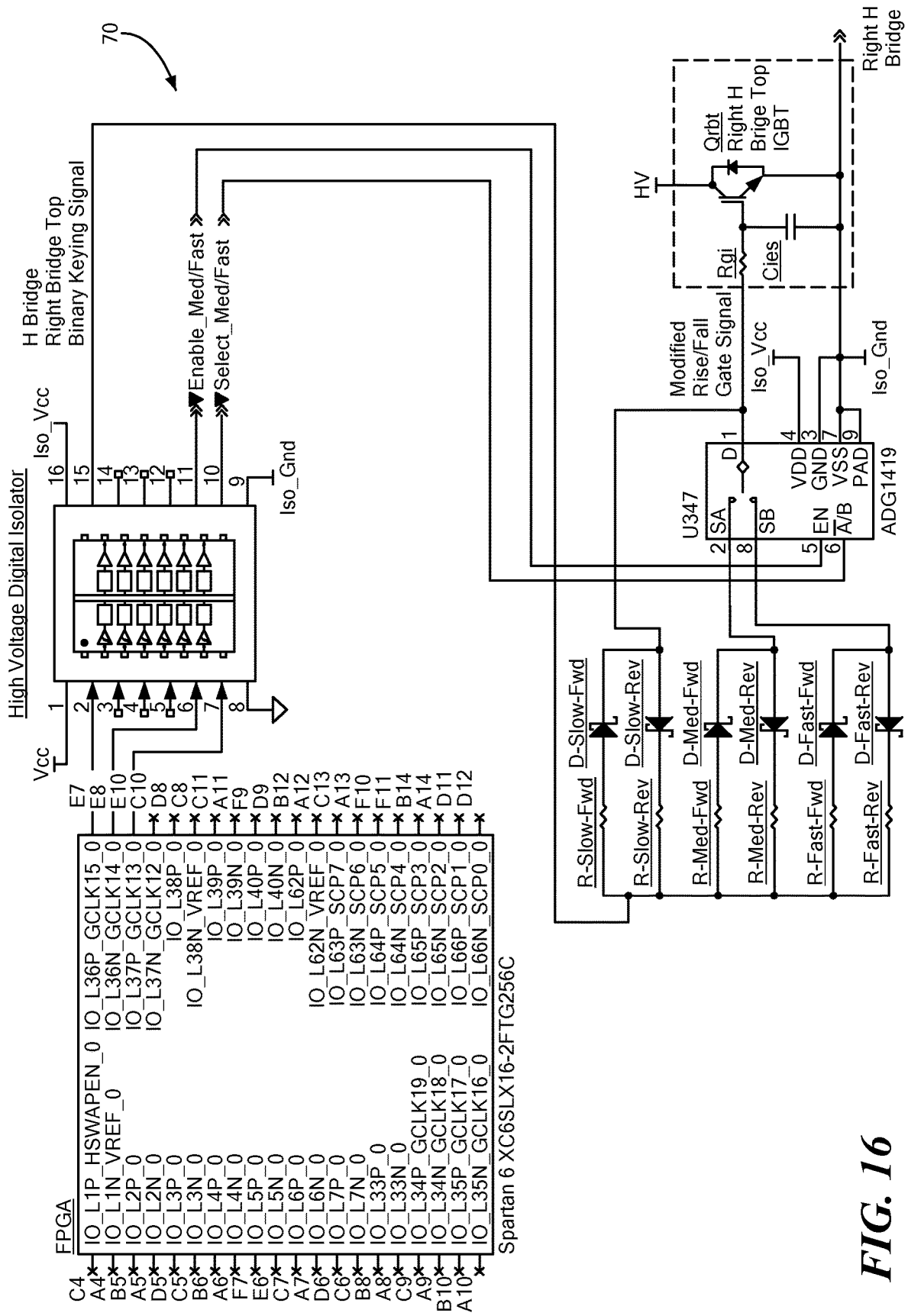
FIG. 16 is a diagram of an exemplary circuit for a PFA system that may be used to adjust rise-fall time.

As noted above, the H bridge circuit 18 may include MOSFETs 20 to create the PFA energy (pulses, such as biphasic pulses). However, insulated gate bipolar transistors (IGBTs) may be used in addition to or instead of MOSFETs 20 in the H bridge. The rise-fall time $\tau$ of high voltage, enhancement mode, MOSFETs or IGBTs in transition from reverse bias to saturation (pulse rising edge) depends primarily on total applied charge and the time rate of change of charge (or current) applied to the gate-emitter junction. To achieve a fully saturated condition, the MOSFET's or IGBT's gate charge requirement increases with increasing emitter-collector current, meaning that if the gate current is limited by a fixed resistance, the device's rise time $\tau_r$ will slow. The effect of this rise time variability is to increase the time in which the electroporation pulse achieves 90% of final amplitude under heavily loaded conditions, such as when gradients between energy delivery electrodes are 1 KV/cm or more. Conversely, if energy delivery electrodes 32 present a lightly loaded condition, the H bridge circuit's 18 collector current is reduced, as is the gate charge requirement. This results in an undesirably fast rise time $\tau_r$ with overshoot and ringing. To compensate for changes in loading such that the rise time $\tau_r$ and/or fall time $\tau_f$ is kept constant, an automatic system of applying fixed, external gate resistances is provided herein. A non-limiting example of a circuit 70 for a PFA system is shown in FIG. 16.

The H bridge circuit 18 may be controlled by the addition of a switch that is operable automatically or semi-automatically to select various discrete values of resistance to add to the H bridge circuit's 18 intrinsic input resistance, which then form a first order low-pass pole with the H bridge circuit's 18 gate or base input capacitance. A formula for the calculation of a typical high voltage switching MOSFET 20 input resistance in the H bridge circuit 18 is given as:

$$\tau_{rise} = \frac{24V}{dQ/dt} = \frac{15V}{147 nC/15 ns} \cong 1.53 \text{ Ohms} \Big|_{Io=25 \text{ amps}} \quad (7)$$

where a charge of 147 nC is necessary to bias the MOSFET 20 for a collector current of 25 amps. For the same representative MOSFET 20, the gate input capacitance is given as 8.56 nF, which for one time constant (63% of steady state)

$$\tau = rc = 1.53 \text{ Ohms} * 3.06 \text{ nF} = 4.7 \text{ ns} \quad (8)$$

Assuming 2.9 time constants, the resulting 10%-90% rise time is 14 ns, which far exceeds the requirement for a PFA system 26.

The rise-fall time ($\tau$ or $\Sigma_r/\tau_f$) of the pulses produced by the PFA generator 22 is maintained within a range of 0.10 μs<$\tau_r/\tau_f$<0.75 μs. Within this range, the rise-fall time is slow enough to avoid poles causing undesired oscillations yet is fast enough to minimize the overall pulse width T needed to achieve electroporative effect. For example, the necessary gate current may be applied using, for example, the circuit shown in FIG. 16. Given varying therapy load conditions (thus currents) that affect the rise/fall time, a master processor unit (MPU) initially provides a known, gate resistance selection via a digital serial word that is sent across a system of isolation gates terminated by a digitally controlled switch. The switch then selects the corresponding resistance (one for forward, the other for reverse bias) and the PFA generator 22 is then prepared for a PFA delivery. Once the first pulse is detected (for example, by the method shown in FIG. 18) and evaluated for its rise-fall time, and that duration falls outside the desired 0.10 μs<$\tau_r/\tau_f$<0.75 μs range, the MPU will send a digital serial word to select a lower-valued resistor pair to decrease, and a higher-valued resistance pair to increase rise time $\tau_r$ and/or fall time $\tau_f$.

Figure 17:
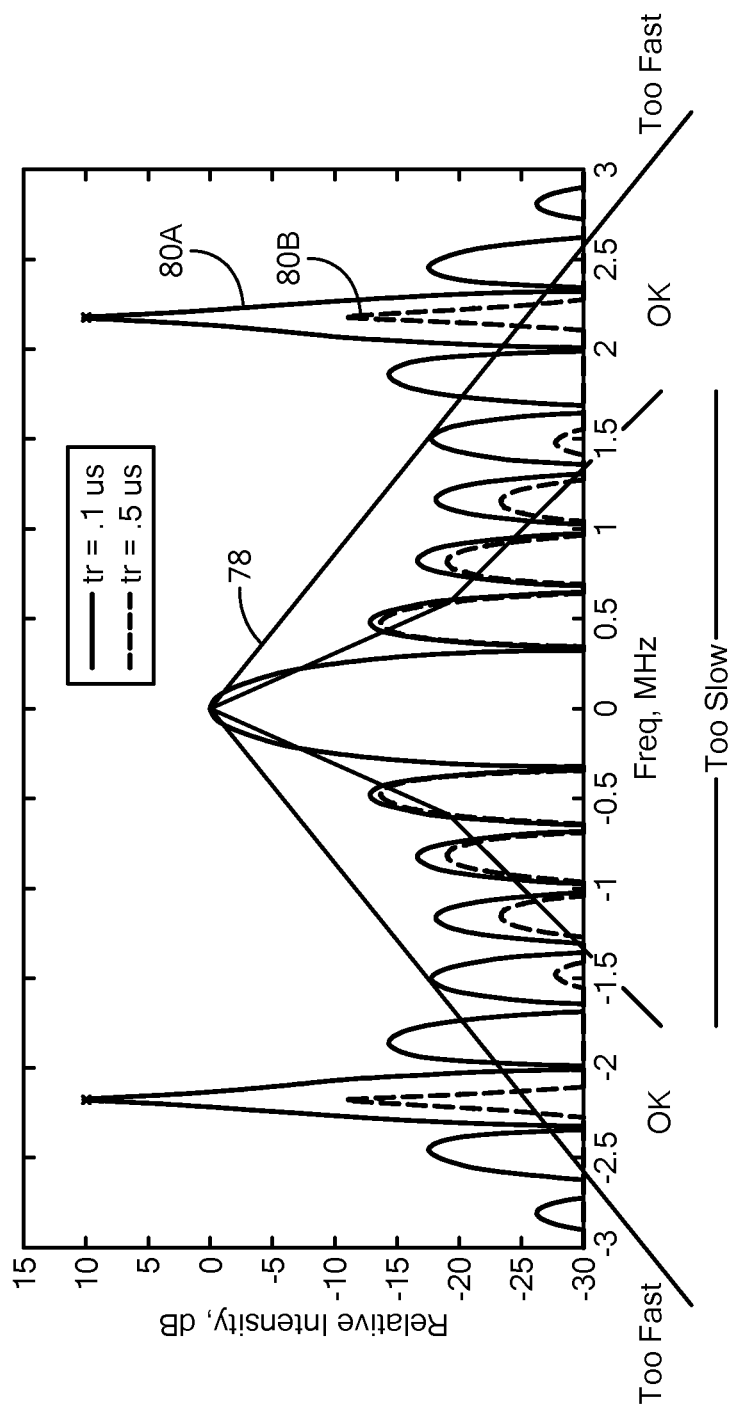
FIG. 17 is a graphical comparison of trapezoidal pulse spectrums (that is, trapezoidal pulses in the spectral domain) with an applied spectral mask.

A third method of reducing ringing (for example, the method shown in FIG. 18) includes applying a spectral mask 78 to a delivered waveform to ensure that the waveform's timing and amplitude characteristics fit the prescribed therapy waveform's dosing prescription. As shown in FIG. 17, the spectral mask 78 consists of an upper boundary and a lower boundary, which contains a compliance region between the two boundaries. The upper boundary limits the trapezoidal pulse spectral amplitude such that if the width of the pulse is too narrow, and/or the rise/fall time is too short, the FFT results will exceed the upper boundary and the pulse width and/or rise/fall time will be increased to compensate the waveform such that on subsequent sampling the spectral response returns to the compliance region. If the spectral response of the pulse falls below the lower boundary, then the pulse width is too long and/or its rise/fall time is too slow such that either or both are shortened, and the spectral response returns inside the compliance region. An exemplary application of a spectral mask 78 applied to a first pulse spectrum 80A with a rise-fall time of τ=0.1 μs and to a second pulse spectrum 80B with a rise-fall time of τ=0.5 μs is shown in FIG. 17. Oscillations and lobes falling outside the spectral mask 78 force a correction into the compliance region. Additionally, the application of the spectral mask 78 facilitates detection of an anomalous pulse before subsequent pulses are delivered that may cause arcing.

A fourth method of reducing ringing and preventing arcing incorporates the first, second, and/or third methods, and further includes adjusting the PFA generator's waveform control, increasing or decreasing the width of delivered pulses, and/or interlocking and ceasing pulse delivery altogether, to eliminate the arc on a subsequent pulse delivery. For example, delivery of the PFA energy may be terminated automatically, semi-automatically, or manually when a determined voltage of the pole(s) is greater than a threshold voltage.

Figure 11:
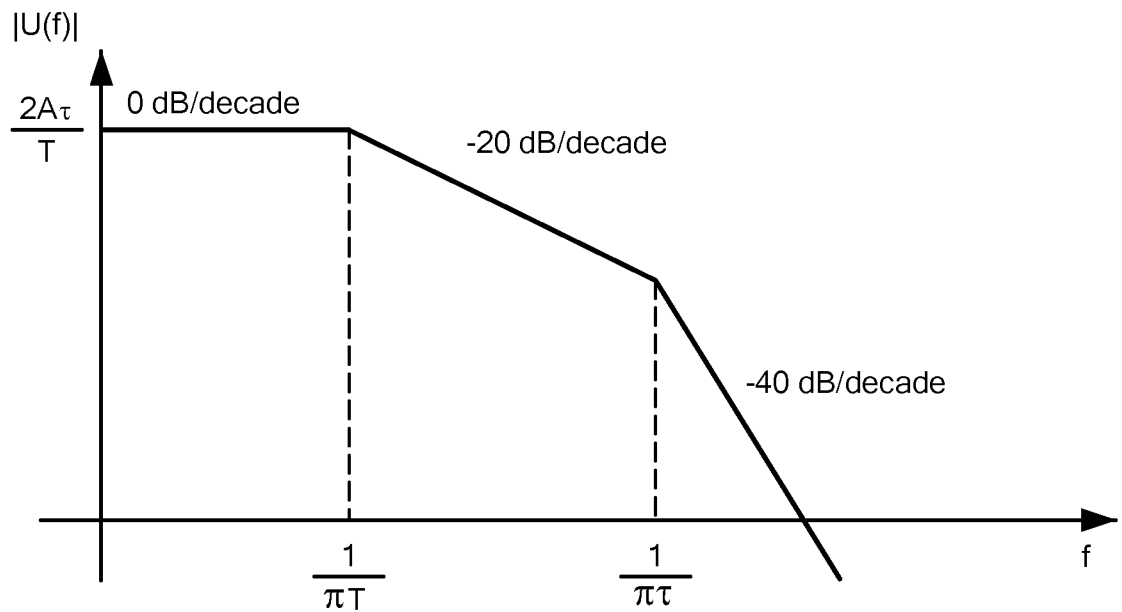
FIG. 11 is a graph showing an exemplary magnitude response in a trapezoidal pulse frequency spectrum.

A fifth method to reduce ringing and prevent arcing incorporates the first, second, third, and/or fourth methods. The synergism of combining these methods can be appreciated by spectral analysis of the therapy generator's trapezoidal waveform. As shown in FIG. 11, the trapezoidal spectrum amplitude is constant over the frequency range:

$$0 < f \leq \frac{1}{\pi T} \text{ Hz} \tag{9}$$

After the first pole at $$f = \frac{1}{\pi T},$$

the spectrum begins to decrease by −20 dB/decade over the range:

$$\frac{1}{\pi T} < f \leq \frac{1}{\pi \tau} \text{ Hz} \tag{10}$$

For frequencies higher than the second pole located at $$f = \frac{1}{\pi \tau},$$

the spectrum decreases at a steeper rate of −40 dB/decade. Therefore, to reduce ringing near the main lobe in the spectral mask 78, it will be more effective to lengthen the pulse width T such that $$f_{ring} > \frac{1}{\pi T}.$$

For higher frequencies, while lengthening T will reduce ringing, a second order effect of −40 dB/decade of attenuation (rather than just −20 dB/decade) can be realized if the rise fall time, τ, is adjusted such that $$f_{ring} > \frac{1}{\pi \tau}.$$

Figure 18:
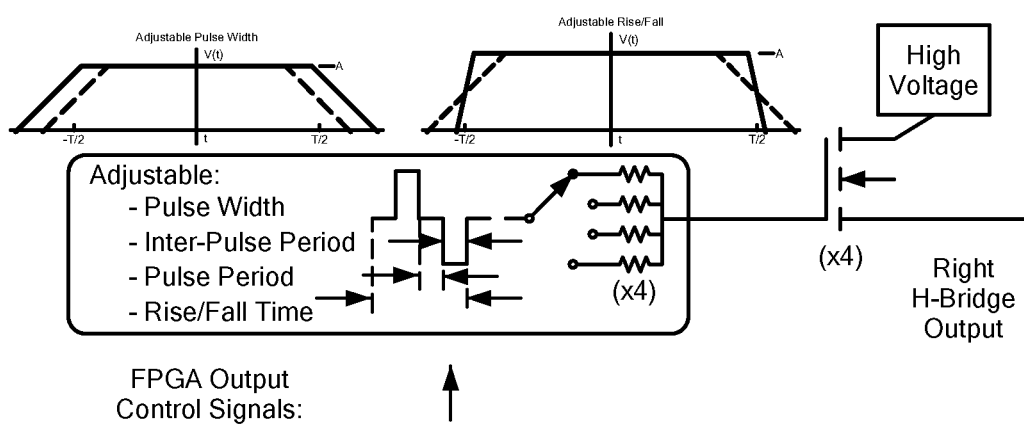
FIG. 18 is an exemplary closed-loop method for performing PFA waveform artifact spectral detection and a correction loop.
Figure 18:
Figure 18:
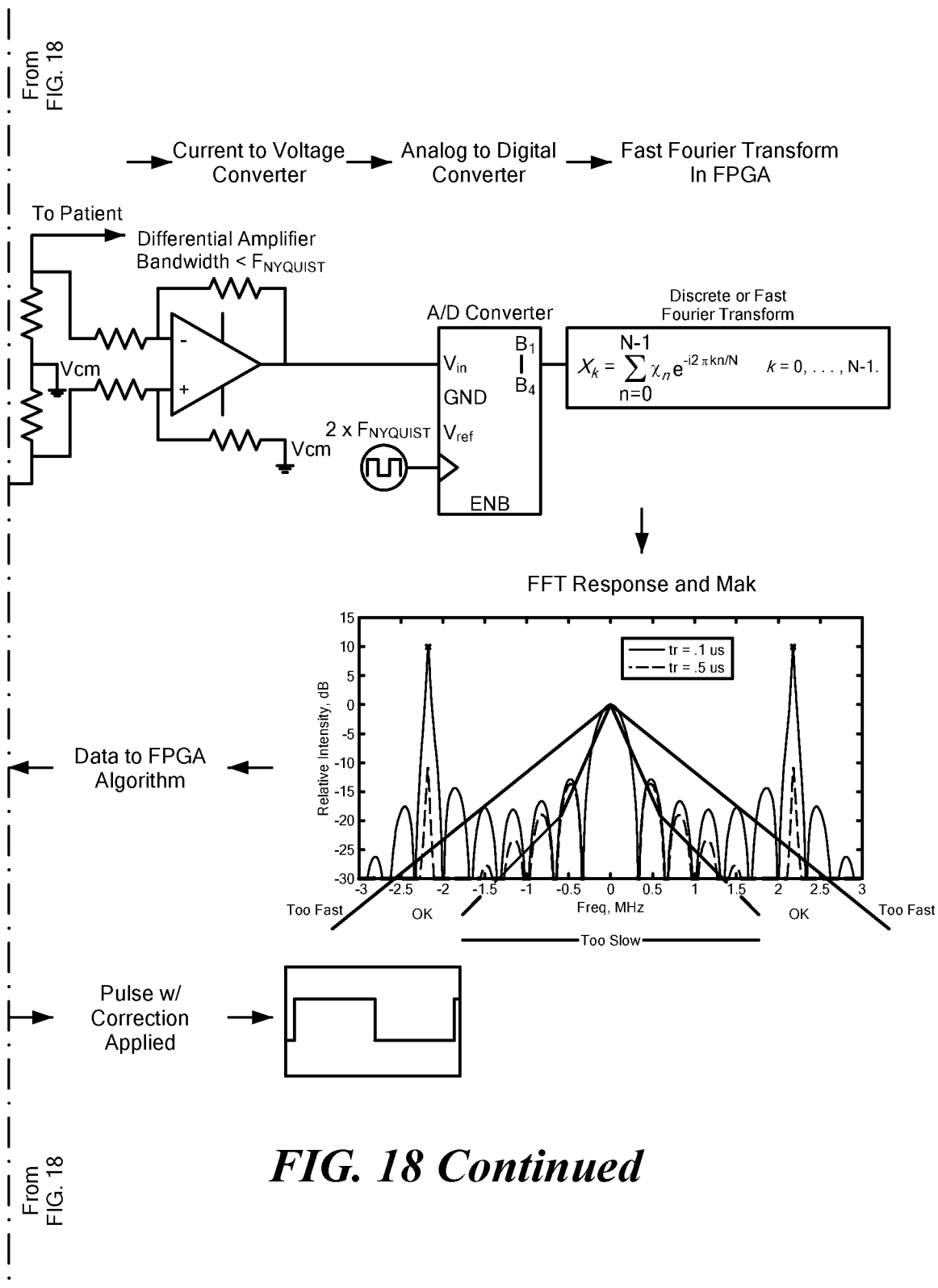
Figure 19:
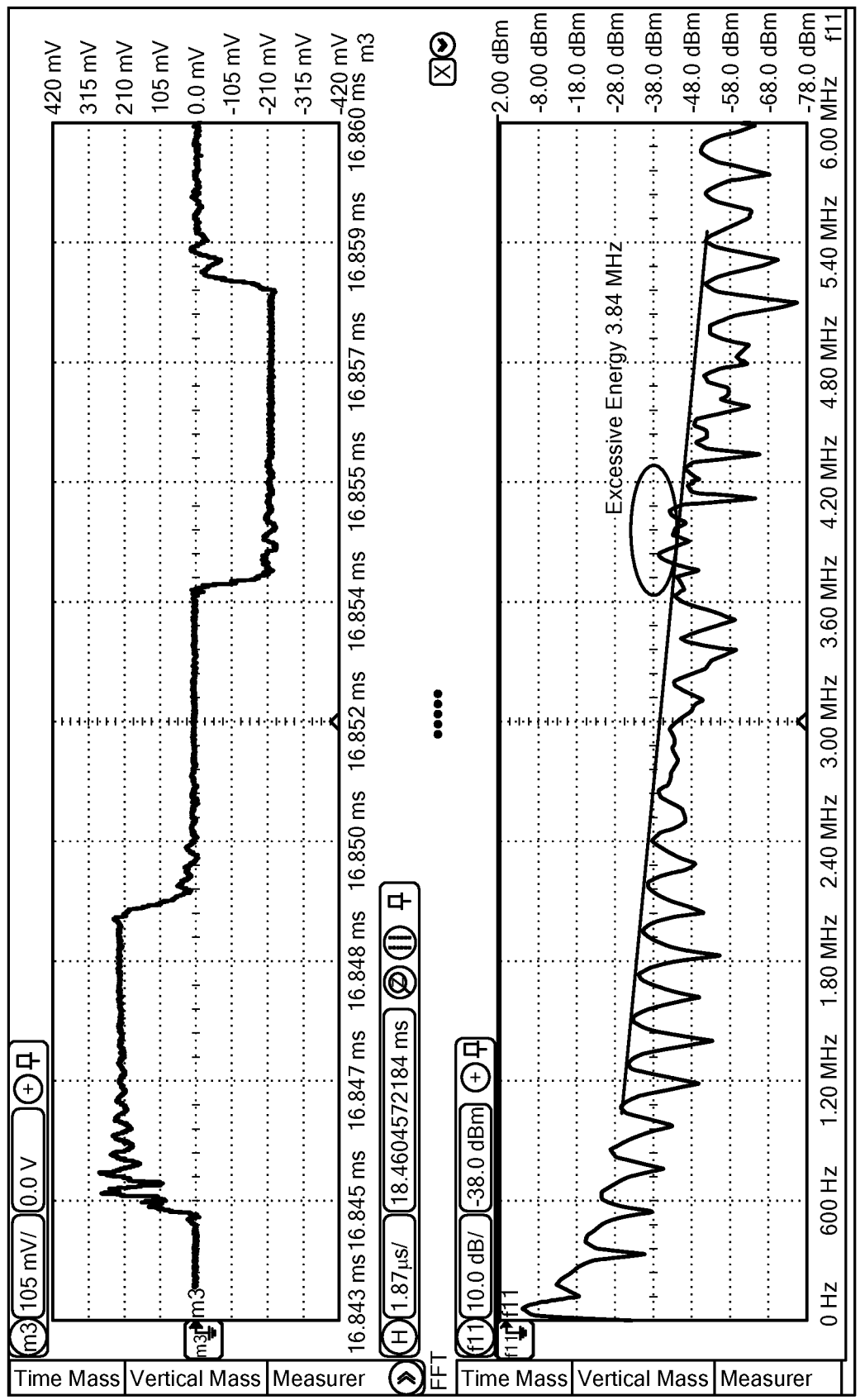
FIG. 19 is an exemplary display showing excessive energy delivery.
Figure 20:
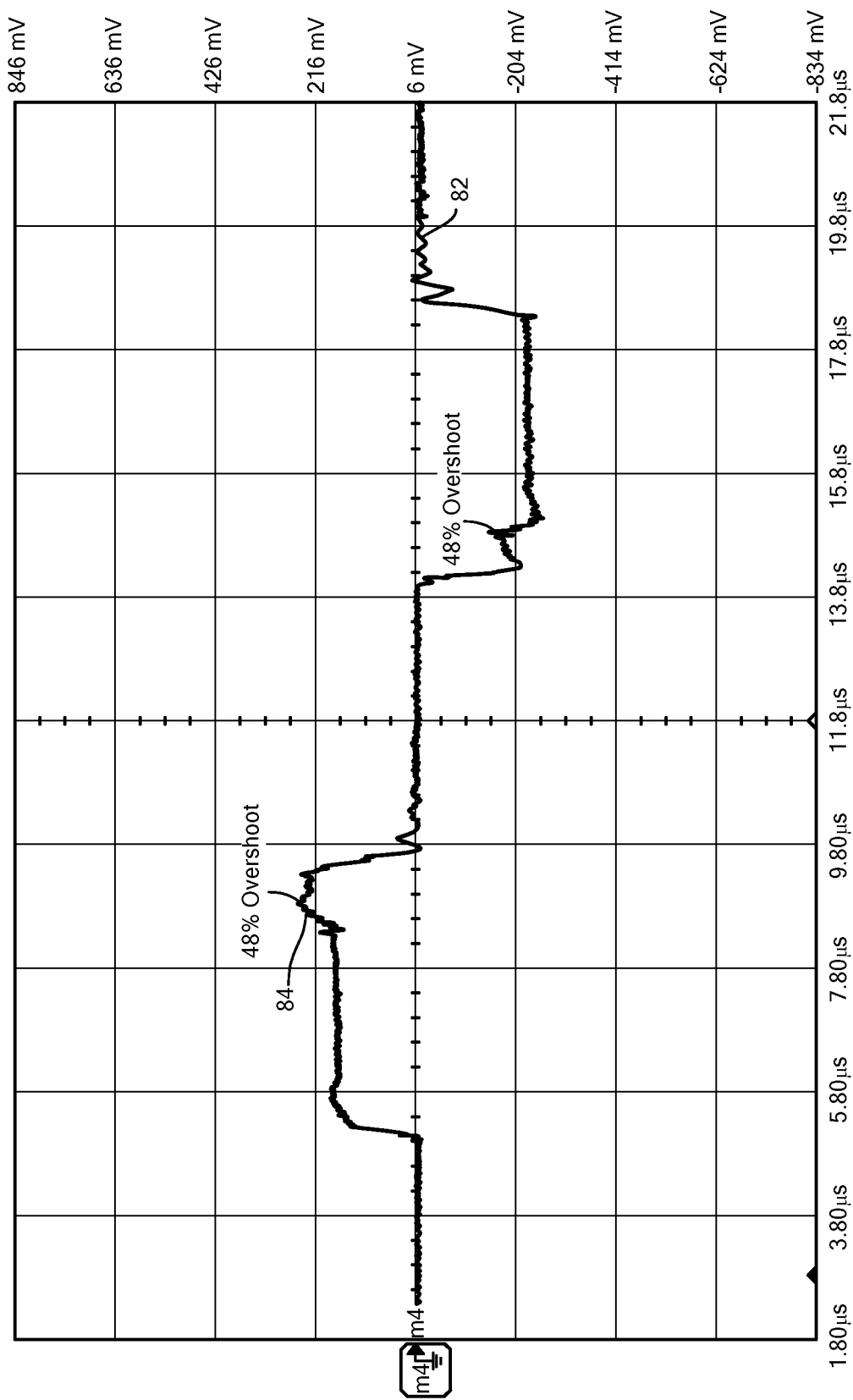
FIG. 20 is an exemplary display showing a pulse with overshoots.
Figure 21:
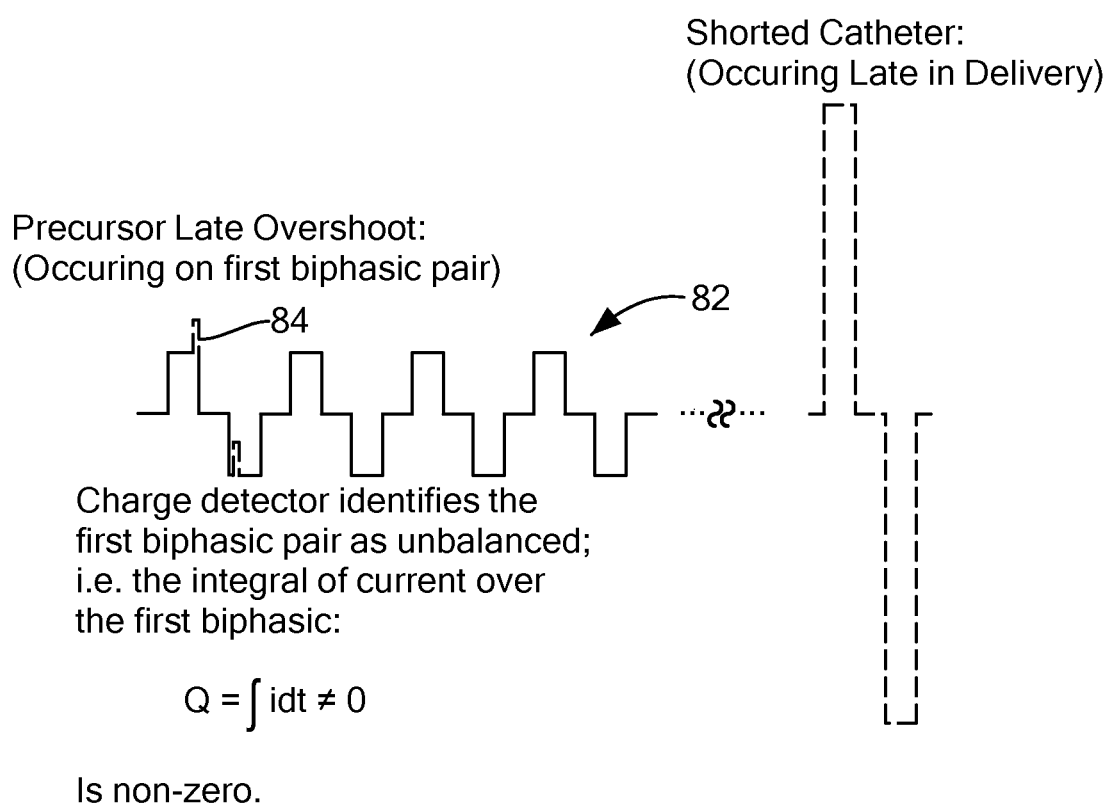
FIG. 21 is an unbalanced biphasic waveform with overshoots.

FIG. 18 shows an overall closed-loop method of generating and sampling the therapy waveform, performing a FFT to decimate spectral content into bins, measuring and determining which bins comply with or fall outside of a desired spectral mask, and increasing or decreasing pulse width and/or pulse rise/fall time. This loop process continues to iterate until the spectral mask goals are met by implying that ringing and arcing are eliminated. If pulse width rise/fall adjustments are unable to correct the waveform, a permanent condition may exist that necessitates generating an electronic message or display to the user that recommends a course of action to remedy an arc condition that may exist due to a damaged or improperly manipulated delivery device 28. For example, the control unit 30 and/or PFA generator 22 may display a visual warning and/or an audible alert to the user recommending the user stop energy delivery because the delivery device 28 is compromised. Additionally or alternatively, the control unit 30 and/or PFA generator 22 may display operating characteristics of the delivery device 28 in real time so the user can identify any impending failure. For example, if the control unit 30 and/or PFA generator 22 determines the delivery device 28 is likely to fail, this may be referred to as a fault condition existing in the delivery device 28. A non-limiting example of such a display is shown in FIG. 19. In the lower portion of the display, the response is approximately +5 dB above nominal at 3.84 MHz, which indicates small arc oscillations are occurring and the delivery device 28 is likely to fail on subsequent energy deliveries. Another non-limiting example of such a display is shown in FIG. 20. On the first pulse, a late overshoot or "hump" is shown, which indicates the delivery device 28 is likely to fail on subsequent energy deliveries. In some embodiments, when the PFA generator 22 detects an overshoot, the amplitude detector 54 automatically terminates energy delivery after the pulse having the overshoot so delivery device 28 failure (for example, a short caused by excessively high current) will not occur. The waveform 82 of the biphasic pulse of FIG. 20, with overshoots 84, and subsequent delivery device 28 failure occurring on a later pulse delivery is shown in FIG. 21. In one example, the PFA generator 22 (for example, a charge detector) identifies a biphasic pulse as unbalanced when the integral of current over the first biphasic pulse has a non-zero value, that is, when:

$$Q = \int i\, dt \neq 0 \tag{9}$$

Figure 22:
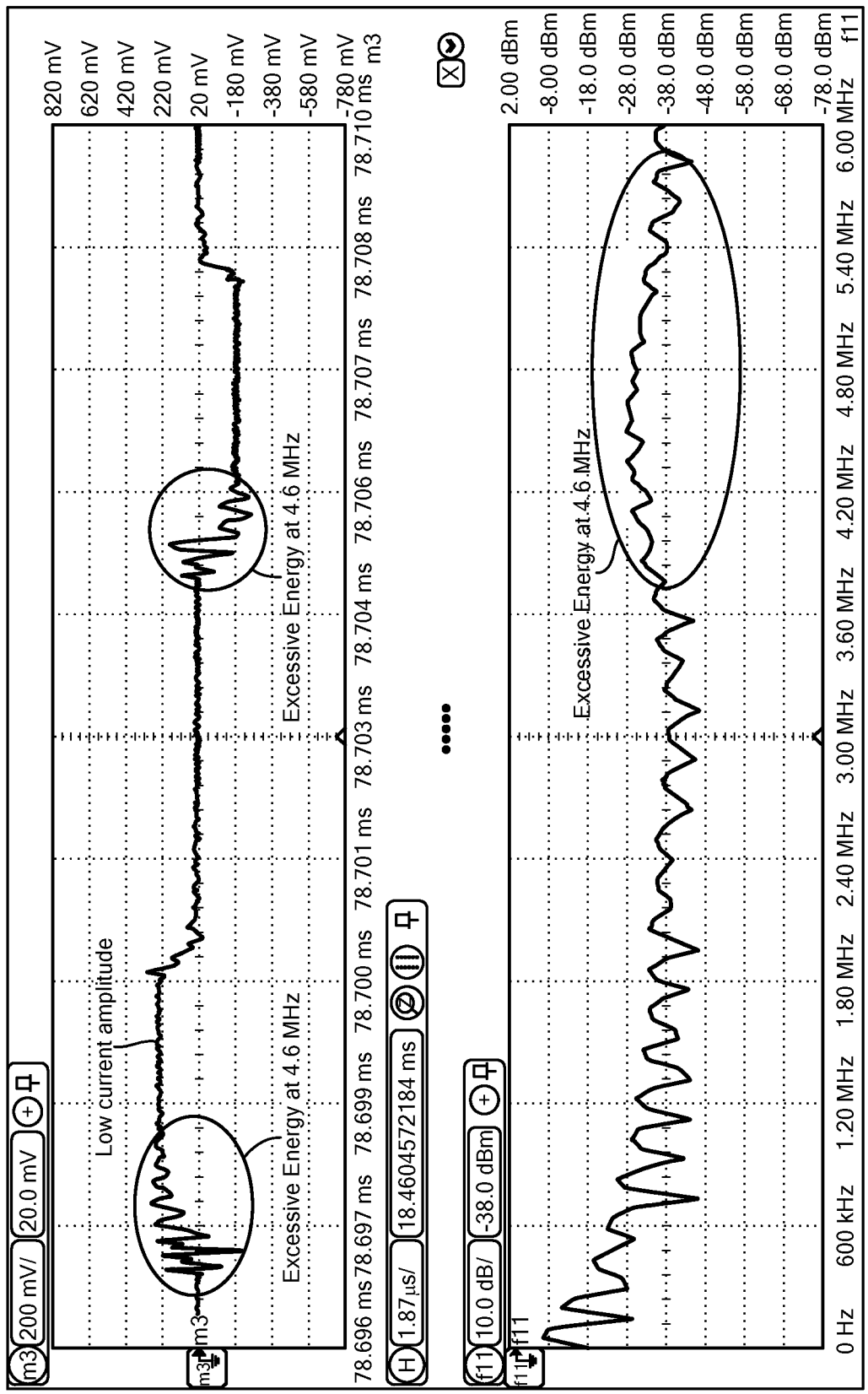
FIG. 22 is an exemplary display showing low current amplitude and excessive energy.
Figure 23:
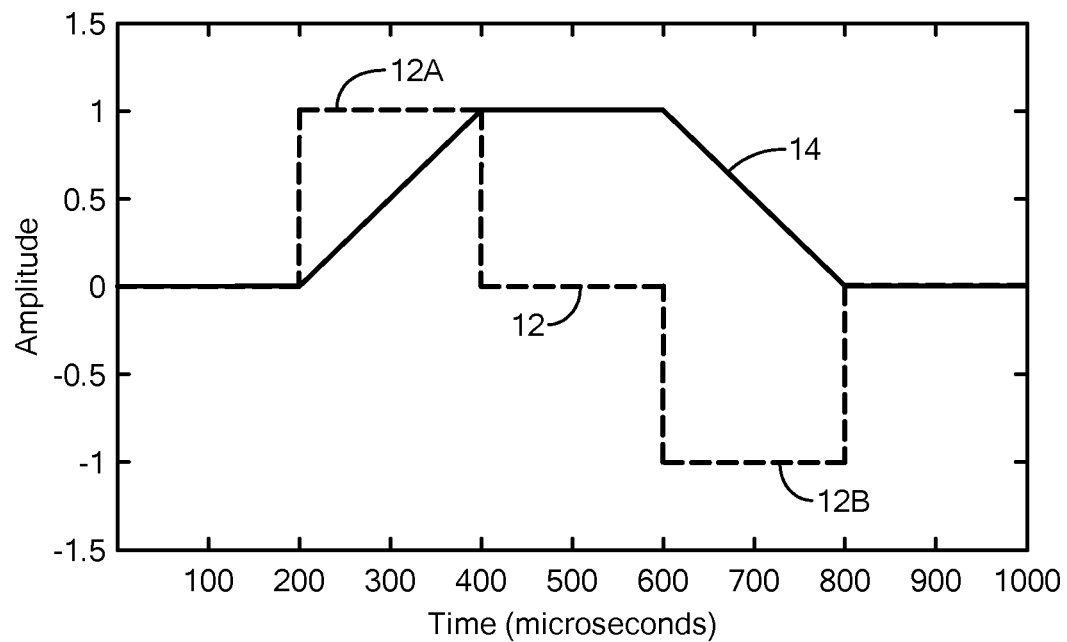
FIG. 23 is a graphical representation of an exemplary ideal biphasic RFA pulse pair, in which both phases have equal and opposite amplitude with instantaneous rise and fall time.
Figure 24:
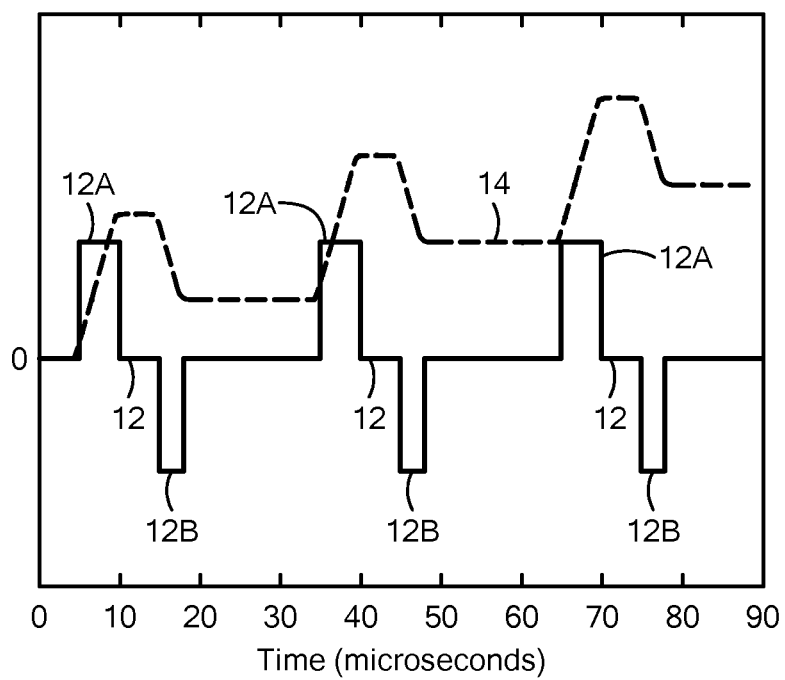
FIG. 24 is a graphical representation of an exemplary asymmetric biphasic pulse that creates net increase in charge delivery after each pulse pair.
Figure 25:
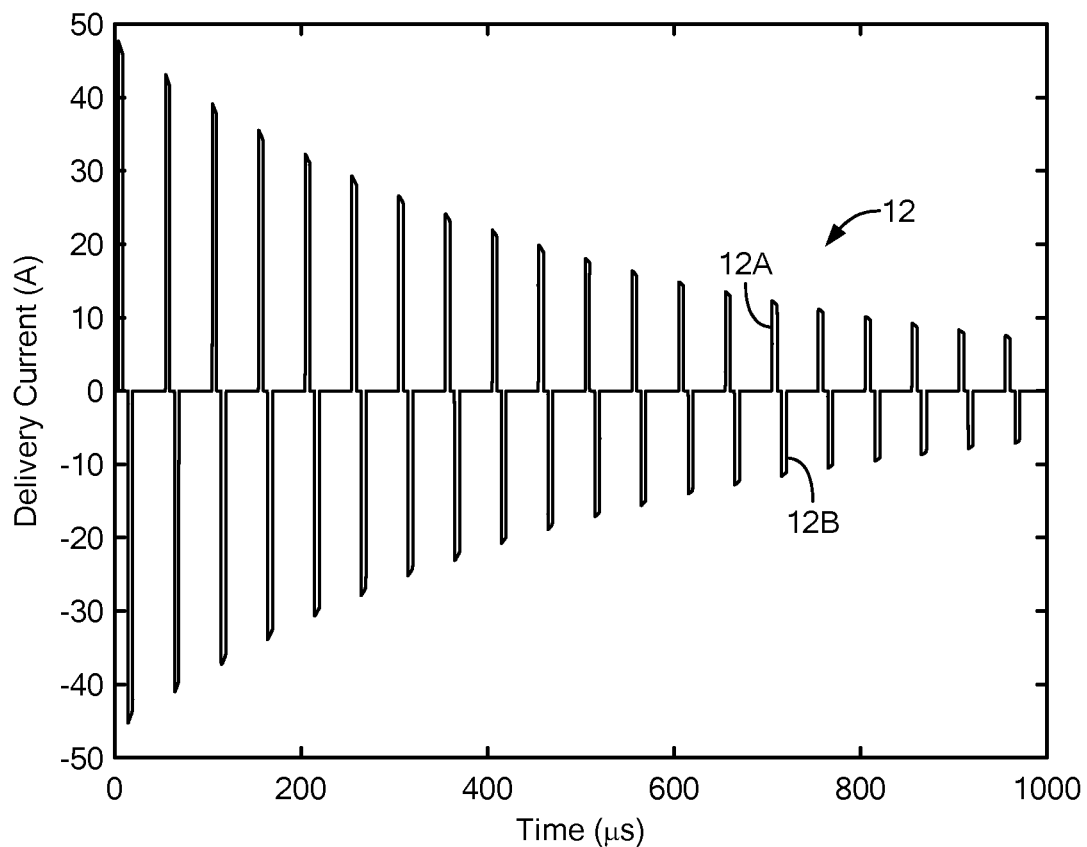
FIG. 25 is a graphical representation of a decrease in output current as energy stored within a capacitor bank is depleted.
Figure 26:
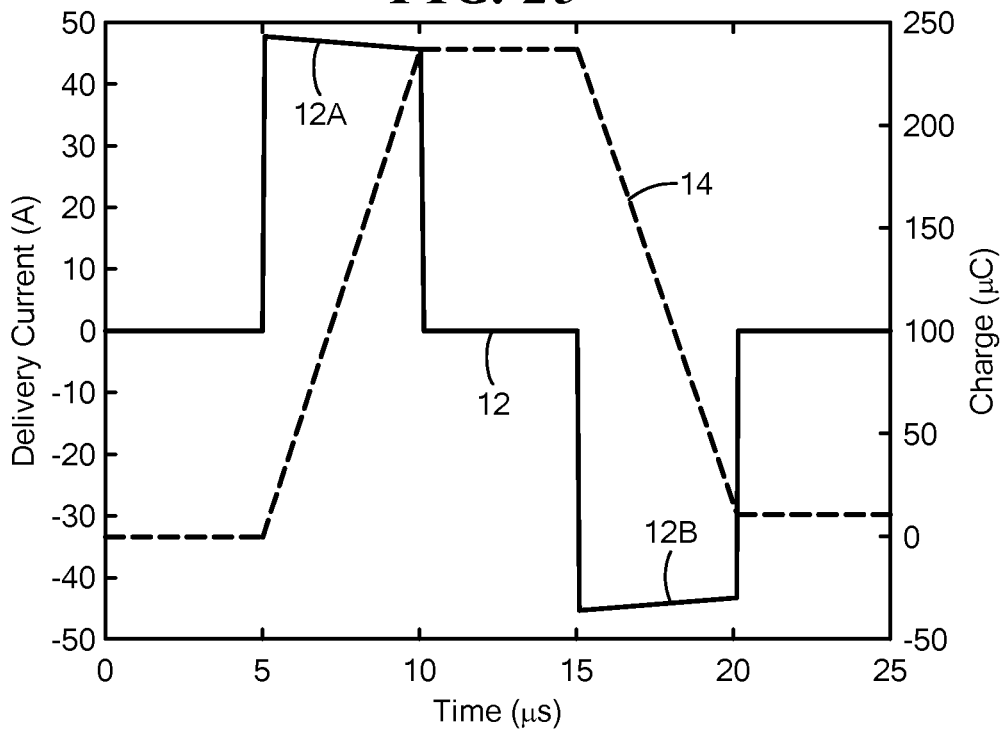
FIG. 26 is a graphical representation of a biphasic pulse with a negative phase and a positive phase, showing an exaggerated, non-limiting example of capacitor bank discharge to provide power for PFA pulse delivery.
Figure 27:
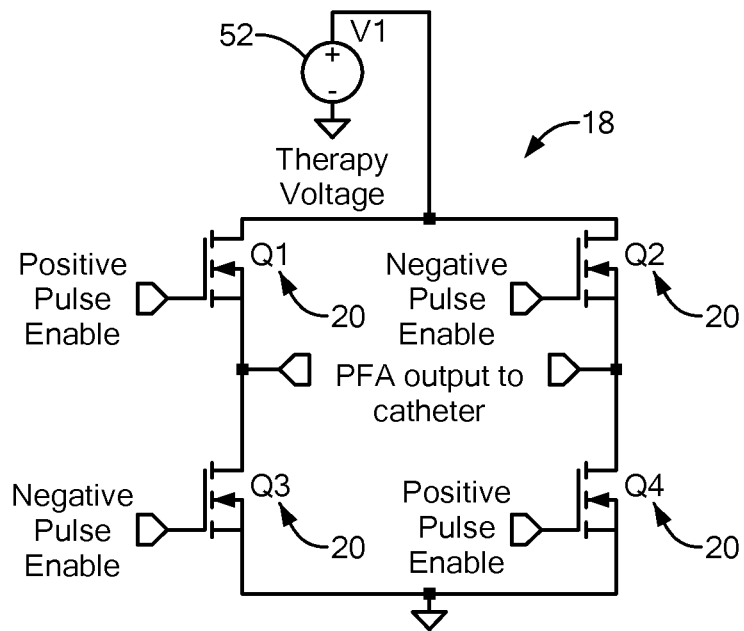
FIG. 27 is a diagram of an exemplary half bridge circuit (H bridge) for delivering PFA energy.

The presence of oscillations in a pulse may also be indicative of misplacement of the energy delivery electrodes 32 within the patient's body. For example, FIG. 22 shows an exemplary display showing a pulse with areas of low current amplitude and excessive energy at 4.6 MHz, which may be caused by overextension of the distal array 40 (and at least one of the energy delivery electrodes 32) of the delivery device 28 into the pulmonary vein when performing a pulmonary vein isolation procedure. Such positioning may increase load resistance, which causes oscillations. In one embodiment, when this occurrence is detected, the user can specify that the system may undergo closed-loop waveform pulse rise-fall and width adjustment, such as is shown in FIG. 18, or the user can elect that the control unit 30 and/or PFA generator 22 provides an alert to adjust the position of the distal array 40 and energy delivery electrodes 32. Additionally, the control unit 30 and/or PFA generator 22 may receive data from one or more sensors 44, such as temperature sensors associated with or in communication with the energy delivery electrodes 32. Temperature data may be displayed by the control unit 30 and/or PFA generator. If temperature sensors record an energy delivery electrode temperature greater than approximately 65° C., the temperature at which soft thrombus (thermal coagulum formation on the energy delivery electrode(s)) occurs, the control unit 30 and/or the PFA generator 22 may delay or prevent energy delivery until the temperature of all energy delivery electrodes 32 falls below 65° C.

Figure 28:
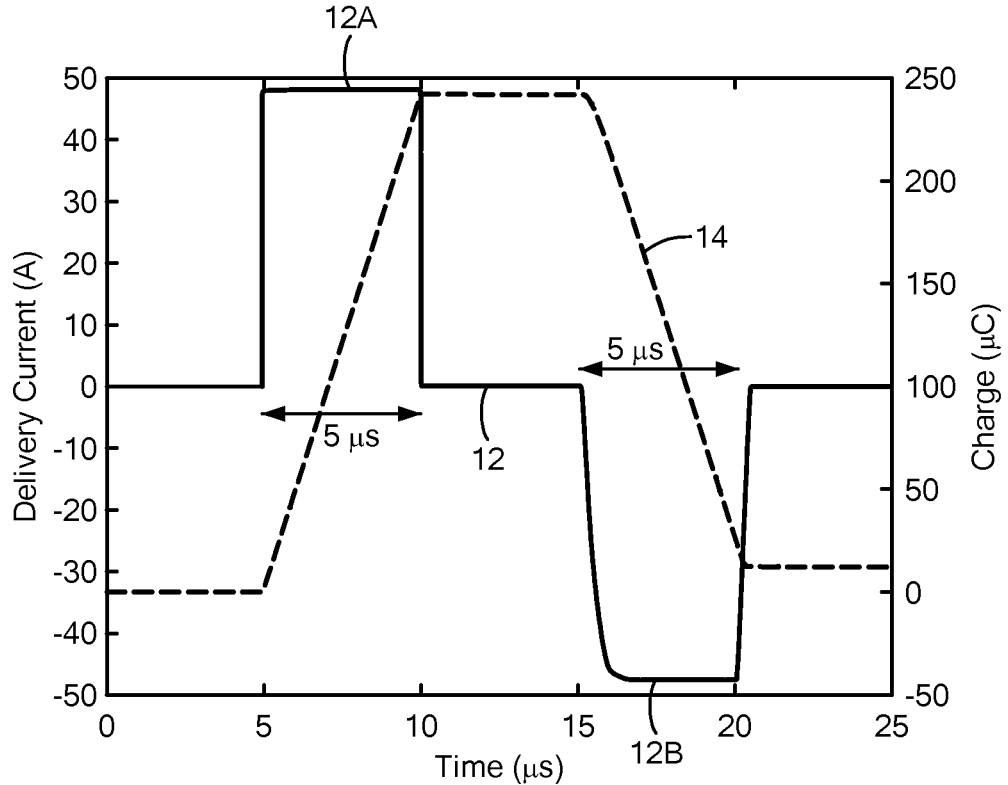
FIG. 28 is a graphical representation of an exemplary biphasic pulse with mismatched rise times between each half of the biphasic pulse, resulting in a net charge imbalance.
Figure 29:
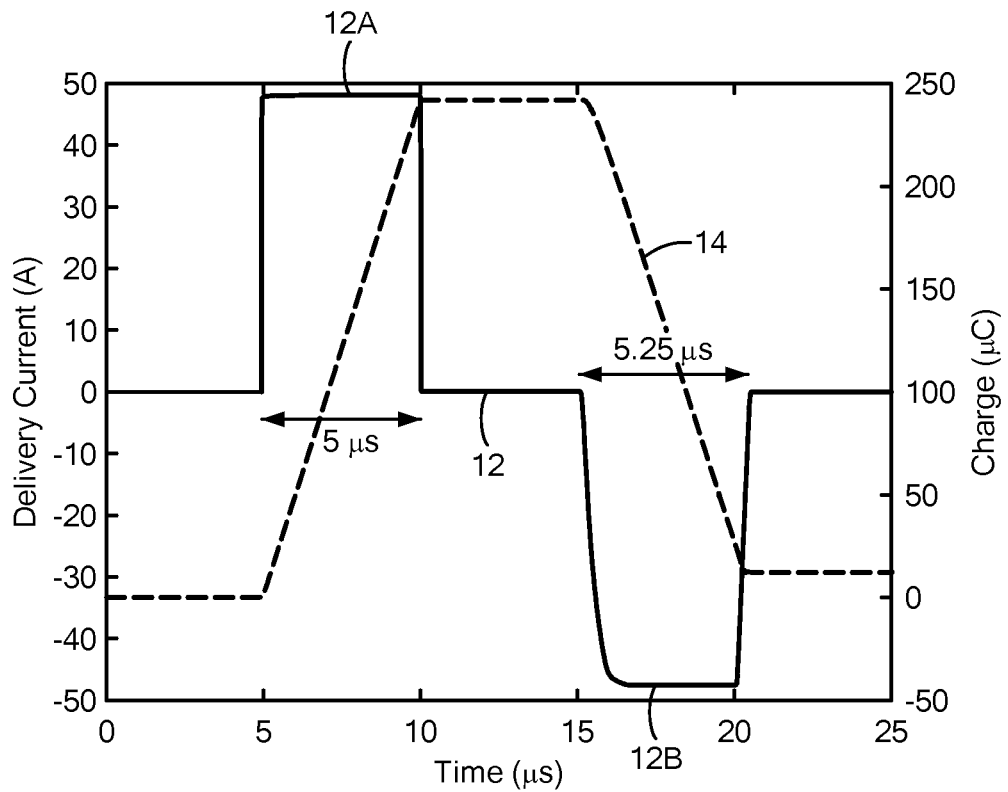
FIG. 29 is a graphical representation of an exemplary biphasic pulse with an adjusted pulse width of the negative phase to correct the net charge imbalance shown in FIG. 24.

As discussed above, biphasic pulse asymmetry during PFA energy delivery may lead to unintended muscle stimulation. Several methods are disclosed herein for correcting charge imbalance or asymmetry. In a first embodiment, a method of correcting charge imbalance includes adjusting the pulse width T of the biphasic pulse. Exemplary ideal PFA pulse pairs have the same pulse width since any difference between the pulse pairs leads to an accumulation of charge. Therefore, adjusting the pulse width can correct such an imbalance. For example, the PFA generator 22 may include a controller that has processing circuitry configured to reduce the pulse width of the overcharged polarity and/or lengthen the pulse width of the undercharged polarity. In the non-limiting example shown in FIG. 28, the negative phase 12B has a slower rise-fall time τ than the positive phase 12A of the pulse 12. To compensate for the resulting charge imbalance, the controller increases the pulse width T by a target amount to effectively balance charge delivery. The pulse width T of the negative phase 12B in FIG. 29 is increased to 5.25 µs, or 250 ns over the pulse width T of 5 µs shown in FIG. 28, resulting in a net charge of zero or approximately zero.

Figure 30:
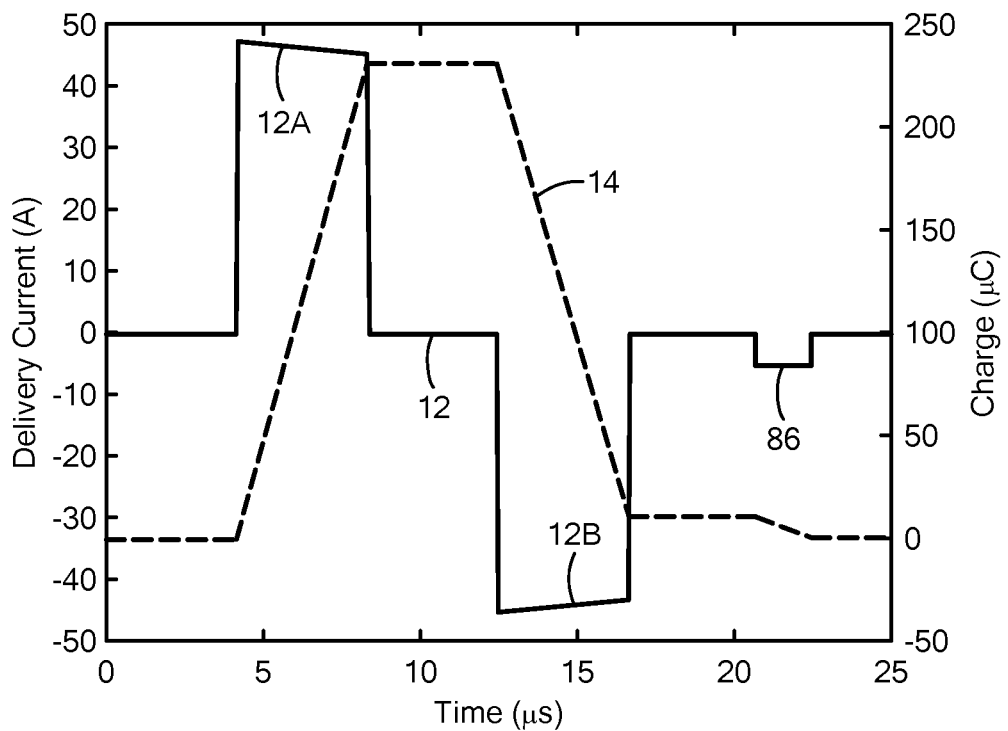
FIG. 30 is a graphical representation of the biphasic pulse of FIG. 22, with an additional runt pulse after the negative phase, resulting in a net charge of zero.
Figure 31:
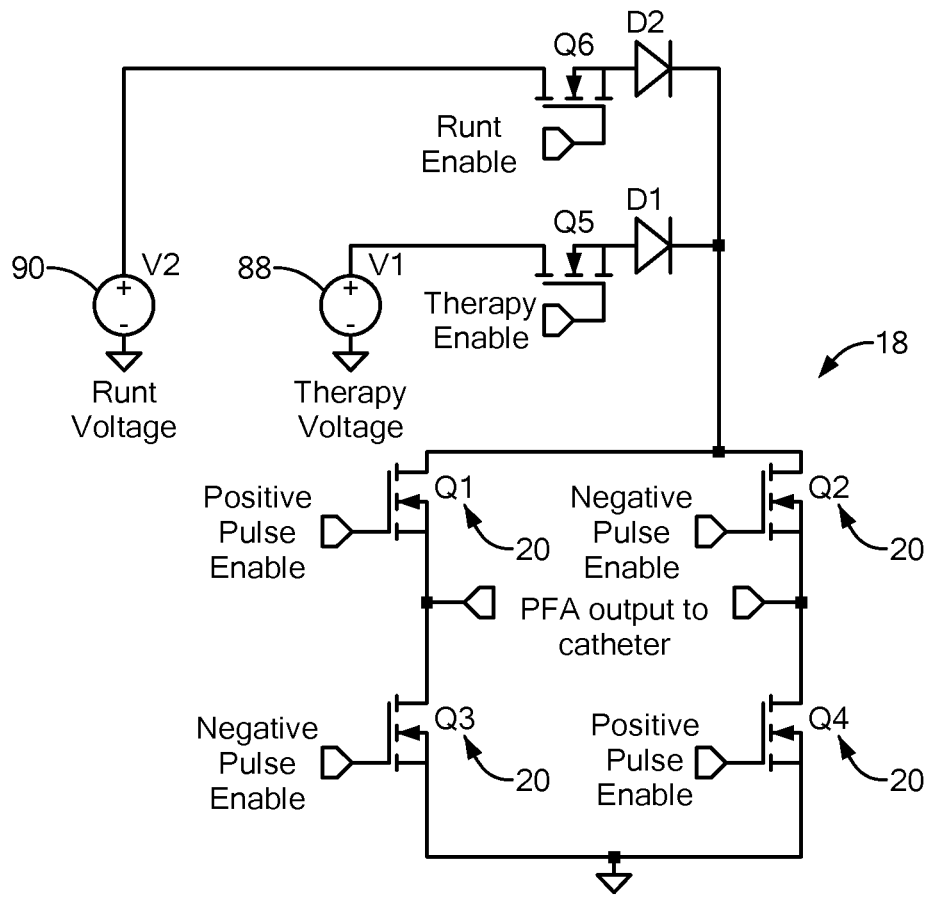
FIG. 31 is a diagram of a H bridge with lower voltage power supply for delivering runt pulses.
Figure 32:
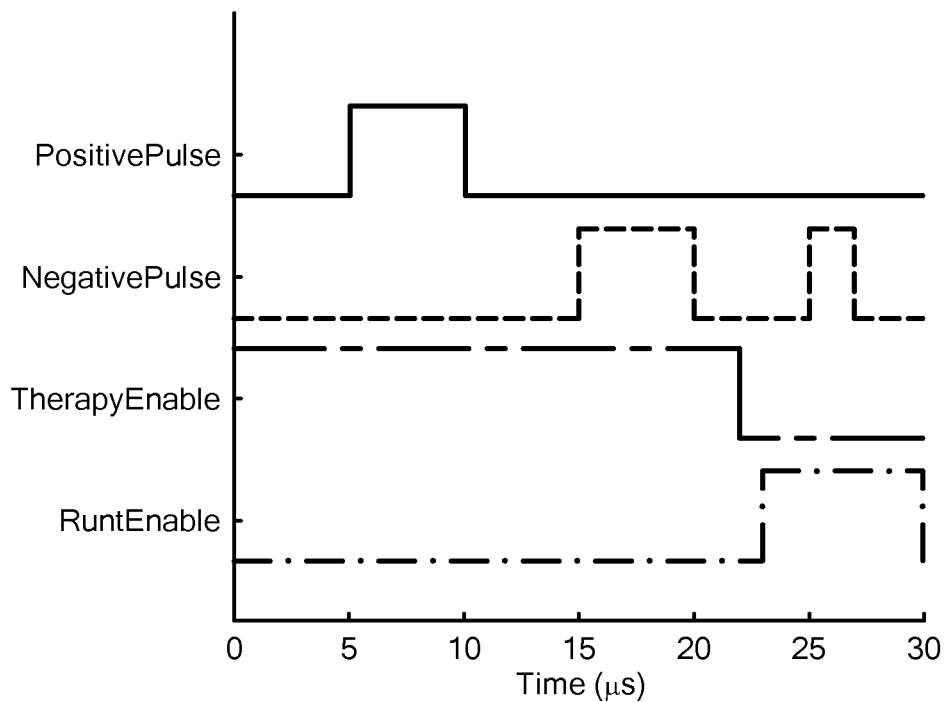
FIG. 32 is a graphical representation of gate voltage applied to each transistor of the H bridge of FIG. 31.

In a second embodiment, the method includes controlling charge buildup by the delivery of lower-voltage "runt" pulses 86. The voltage of these runt pulses 86 must be high enough to delivery sufficient balancing energy in a timely manner, yet must be low enough to avoid electroporative effects, both reversible and irreversible. For example, it is important to avoid causing irreversible electroporation with runt pulses so the dosing level of the PFA therapy remains constant. Likewise, although the effects of reversible electroporation are temporary, they may change a patient's electrocardiograms in ways that may mislead the physician. FIG. 30 shows an exemplary biphasic pulse 12 including a runt pulse 86 following the negative phase 12B. Inclusion of the runt pulse 86 results in a net charge of zero or approximately zero. Implementing runt pulse delivery requires a lower voltage power supply in addition to the high-voltage therapy power supply, and must include a way to switch between the two power supplies while avoiding interference between them. FIG. 31 shows an exemplary H bridge 18 with a high-voltage power source 88 for delivering therapy pulses and a lower-voltage power source 90 for delivering runt pulses 86, and FIG. 32 shows a gate voltage applied to each transistor of the H bridge of FIG. 31. During therapy, the "Therapy Enable" signal on the gate of Q5 allows it to conduct, providing high voltage from the high-voltage power source 88 to the H bridge 88 and, ultimately, to the patient. If charge balancing is needed, the "Therapy Enable" signal is de-asserted and the "Runt Enable" signal is asserted instead. This allows the H bridge 18 to deliver lower runt voltage to the patient to balance charge as described above.

The PFA generator's 22 controller may implement either an open-loop control scheme or a closed-loop control scheme. An open-loop control scheme determines how much influence to exert on the PFA system 26 without measuring the amount of charge delivered, whereas a closed-loop control scheme adjusts the PFA generator's 22 output based on the actual amount of charge delivered to the patient.

In an open-loop control scheme, the controller simply chooses how much to influence the charge and exerts that much control, such as through adjusting pulse width T or runt pulse delivery. The controller may also prompt and/or require the user to adjust the PFA generator's 22 output. Such a system may work best if the source of the charge imbalance is well characterized. For example, the effect of discharging a capacitor bank is well understood, and therefore is relatively easily compensated for by the controller. The charge imbalance resulting from each pulse may be calculated using the equations below, with the necessary runt pulse parameters to equalize the imbalance. Equation 9 represents the charge imbalance due to pulse pair number n:

$$\Delta Q_n = C \times V_0 \times \left( e^{-\frac{(2n-2) \times T}{R \times C}} - 2e^{-\frac{(2n-1) \times T}{R \times C}} + e^{-\frac{2n \times T}{R \times C}} \right) \quad (9)$$

and Equation 10 represents the runt pulse width $T_{runt}$ needed to balance the charge due to pulse number n:

$$T_{runt} = \frac{\Delta Q_n \times R}{V_{runt}} \quad (10)$$

where $\Delta Q_n$ is the difference in charge resulting from pulse pair n, C is the capacitance in Farads of the capacitor bank, $V_0$ is the initial therapy voltage, n is the number of the pulse pair requiring the balance, T is the pulse width in seconds of each therapy pulse, R is the combined tissue and delivery device impedance, $T_{runt}$ is the pulse width in seconds of the runt pulse needed to balance the charge, and $V_{runt}$ is the voltage of the runt pulse.

Equations 9 and 10 depend on the load impedance seen by the PFA system 26, which value may be obtained prior to delivery by use of an impedance meter or during delivery by monitoring therapy current during the first pulse before the capacitor bank has discharged significantly. Alternatively, the PFA system 26 (for example, the controller of the PFA generator 22) may simply estimate the impedance based on known values, such as delivery device 28 type and energy delivery electrode 32 selection.

Figure 33:
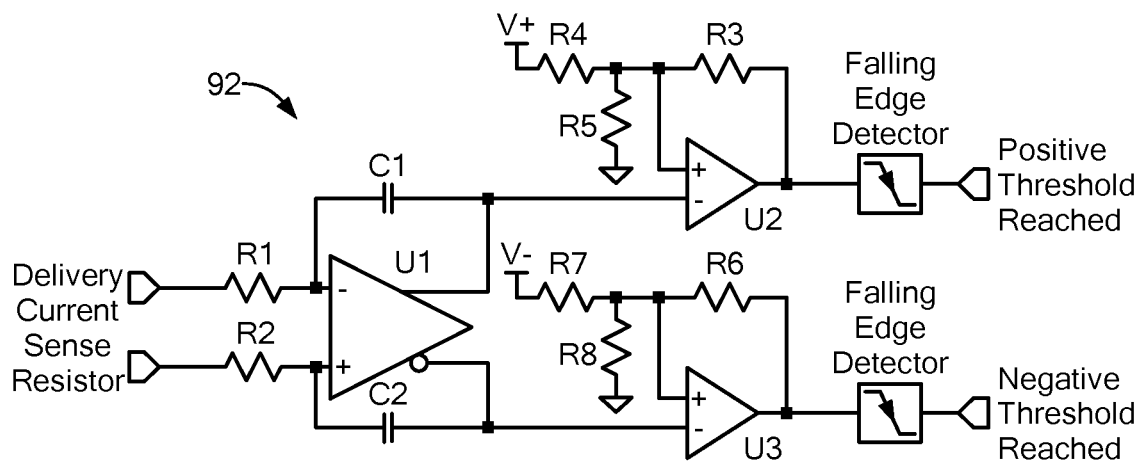
FIG. 33 is a diagram of an exemplary circuit for providing feedback in a closed-loop control system.

In a closed-loop control scheme, the controller includes sensors or detectors that monitor the amount of charge delivered and/or an integral of that charge and provide feedback to the H bridge circuit 18. The H bridge circuit 18 uses data received by the sensors to dynamically tune the amount of charge compensation provided, either automatically or semi-automatically (for example, at user initiation). An exemplary circuit 92 used to provide such feedback is shown in FIG. 33. The circuit 92 of FIG. 33 dynamically monitors charge delivered to the patient and sends a digital pulse when the accumulated charge returns to zero after having first risen past a threshold value. The control unit 30 and/or PFA generator 22 can use this digital pulse as feedback to indicate when the runt pulse or pulse width adjustment has fully balanced the charge. In one embodiment, the circuit 92 sends a digital pulse within a predetermined time period before the charge returns to zero to account for delays while the controller reacts to the digital signal.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of modifying pulsed field ablation (PFA) energy delivery, the method comprising:
    delivering a PFA pulse from a PFA generator;
    determining, with an amplitude detector, a 10% amplitude and a 90% amplitude of a final amplitude of the PFA pulse in the time domain;
    measuring, with a counter circuit, a rise time and a fall time of the PFA pulse based on the 10% amplitude and the 90% amplitude of the final amplitude;
    calculating a voltage of at least one oscillatory pole in the PFA pulse based at least in part on the rise time and the fall time; and
    modifying a pulse width of the PFA pulse and at least one of the rise time and the fall time to reduce the voltage of the at least one oscillatory pole in the PFA pulse, wherein modifying the pulse width and at least one of the rise time and the fall time includes
    generating, with the counter circuit and the amplitude detector, a correction signal based on the rise time and the fall time, and
    applying the correction signal to the PFA generator.

2. The method of claim 1, wherein the PFA generator further includes processing circuitry having an H bridge circuit.

3. The method of claim 2, wherein modifying the at least one of the rise time and the fall time includes applying the correction signal to adjust an input resistance in the H bridge circuit.

4. The method of claim 1, wherein modifying at least one of the rise time and the fall time includes reducing the time in which the PFA pulse reaches 90% of a final amplitude of the PFA pulse when gradients between energy delivery electrodes are 1 KV/cm or more.

5. The method of claim 1, wherein the at least one of the rise time and the fall time is modified to a time between 0.3 µs and 0.5 µs.

6. The method of claim 1, further comprising:
    measuring a pulse width of the PFA pulse;
    calculating a voltage of an oscillatory pole in the PFA pulse based at least in part on the pulse width; and
    modifying the pulse width to reduce the voltage of the at least one oscillatory pole in the PFA pulse.

7. The method of claim 1, further comprising:
    ceasing delivery of the PFA pulse from the PFA generator when the calculated voltage of the oscillatory pole is greater than a threshold voltage.

8. A method of modifying pulsed field ablation (PFA) energy delivery, the method comprising:
    delivering at least one biphasic PFA pulse from a PFA generator, each of the at least one biphasic PFA pulse including a biphasic pair having a positive phase and a negative phase;
    determining, with an amplitude detector, a 10% amplitude and a 90% amplitude of a final amplitude of the PFA pulse in the time domain;
    measuring, with a counter circuit, a rise time and a fall time of the PFA pulse based on the 10% amplitude and the 90% amplitude of the final amplitude;
    calculating a value of an integral of a current over the biphasic pair;
    calculating a voltage of at least one oscillatory pole in the PFA pulse based at least in part on the rise time and the fall time; and
    modifying a pulse width of the PFA pulse and at least one of the rise time and the fall time to reduce the voltage of the at least one oscillatory pole in the PFA pulse, wherein modifying the pulse width and at least one of the rise time and the fall time includes
    generating, with the counter circuit and the amplitude detector, a correction signal based on the rise time and the fall time, and
    applying the correction signal to the PFA generator.

9. The method of claim 8, further comprising:
    measuring a pulse width of the PFA pulse; and
    modifying the pulse width of the biphasic PFA pulse when the integral of the current has a non-zero value.

10. The method of claim 9, further comprising delivering a runt pulse in the biphasic PFA pulse and modifying the pulse width of the biphasic PFA pulse when the integral of the current has a non-zero value.

11. The method of claim 10, wherein the runt pulse has an amplitude that is less than an amplitude of the positive phase of the biphasic pair.

12. The method of claim 10, wherein the runt pulse has an amplitude that is less than an amplitude of the negative phase of the biphasic pair.

13. The method of claim 10, wherein the runt pulse is delivered after the negative phase of the biphasic pair.

14. The method of claim 1, wherein modifying at least one of the rise time and the fall time includes applying a spectral mask to a delivered waveform to ensure that the timing of the waveform and amplitude characteristics fit a prescribed dosing prescription of the waveform, wherein the mask includes an upper boundary, a lower boundary, and a compliance region between the upper boundary and the lower boundary.

* * * * *